(12) United States Patent
Salamone et al.

(10) Patent No.: US 7,795,326 B2
(45) Date of Patent: Sep. 14, 2010

(54) CONFORMABLE BANDAGE AND COATING MATERIAL

(75) Inventors: Joseph C. Salamone, Boca Raton, FL (US); Ann Beal Salamone, Boca Raton, FL (US); Marcus J. Lowe, Miami, FL (US)

(73) Assignee: Rochal Industries, LLP, San Antonio, TX (US)

( * ) Notice: Subject to any disclaimer, the term of this patent is extended or adjusted under 35 U.S.C. 154(b) by 0 days.

(21) Appl. No.: 11/565,453

(22) Filed: Nov. 30, 2006

(65) Prior Publication Data

US 2007/0129474 A1 Jun. 7, 2007

Related U.S. Application Data

(60) Provisional application No. 60/742,965, filed on Dec. 7, 2005.

(51) Int. Cl.
*A61F 13/02* (2006.01)

(52) U.S. Cl. ............... 523/118; 424/447; 424/443; 424/486; 424/78.06; 602/52; 604/304; 128/DIG. 21; 524/268; 524/269; 524/424; 524/462; 524/547; 524/555; 526/279

(58) Field of Classification Search ............... 523/118; 526/279; 424/447, 443, 486, 78.06; 602/52; 604/304; 128/DIG. 21; 524/268, 269, 424, 524/462, 547, 555
See application file for complete search history.

(56) References Cited

U.S. PATENT DOCUMENTS

| | | | | |
|---|---|---|---|---|
| 3,202,919 A | * | 8/1965 | Kitz et al. ............ 327/183 |
| 4,062,451 A | * | 12/1977 | Gander .............. 206/524.2 |
| 4,981,903 A | * | 1/1991 | Garbe et al. ........... 524/547 |
| 4,987,893 A | | 1/1991 | Salamone et al. |
| 5,103,812 A | * | 4/1992 | Salamone et al. ....... 602/52 |
| 5,589,108 A | * | 12/1996 | Shimizu et al. ......... 252/500 |
| 5,667,771 A | * | 9/1997 | Carballada et al. ..... 424/70.12 |
| 5,696,193 A | * | 12/1997 | Daniel et al. ........... 524/408 |
| 6,020,445 A | * | 2/2000 | Vanderlaan et al. ..... 526/279 |
| 6,022,330 A | | 2/2000 | Chen et al. |
| 6,143,805 A | | 11/2000 | Hickey et al. |
| 6,183,593 B1 | | 2/2001 | Narang et al. |
| 6,358,503 B1 | | 3/2002 | Gerrish |
| 6,383,502 B1 | * | 5/2002 | Dunshee et al. ........... 424/401 |
| 6,451,429 B2 | | 9/2002 | Mumick et al. |
| 6,503,494 B1 | * | 1/2003 | Cauwet-Martin et al. .. 424/70.1 |
| 6,548,596 B1 | * | 4/2003 | Kohr et al. ................. 524/800 |
| 6,638,991 B2 | * | 10/2003 | Baba et al. ................. 522/99 |
| 6,669,752 B2 | * | 12/2003 | Arnold et al. .............. 71/27 |
| 6,750,352 B2 | * | 6/2004 | Ono et al. ............. 548/341.5 |
| 6,833,408 B2 | | 12/2004 | Sehl et al. |
| 6,976,997 B2 | * | 12/2005 | Noolandi et al. ......... 623/5.14 |
| 7,247,672 B2 | * | 7/2007 | Tamazawa ................ 524/588 |
| 7,318,937 B2 | * | 1/2008 | Jonn et al. ................ 424/487 |

OTHER PUBLICATIONS

Annaka, et al., "Study on the rapid deswelling mechanism of comb-type N-isopropylacrylamide gels", Colloids and Surfaces B: Biointerfaces, 38(3,4): 201-7 (2004).

Bergbreiter, et al., "Sequestration of Trace Metals Using Water-Soluble and Fluorous Phase-Soluble Polymers", Agnew. Chem. Int. Ed. 39(6): 1039-1042 (2000).

Kim, et al., "Synthesis and Charcterization of Poly(N-isopropylacrylamide) Containing Polydimethylsiloxane", Journal of the Korean Chemical Society, 45(3): 230-5 (2001).

Liu, et al., "The effect of salt and pH on the phase-transition behaviors of temperature-sensitive copolymers based on . . . ", Biomaterials, 25(25): 5659-659 (2004).

Ohya, et al., "The potential of poly(N-isopropylacrylamide) (PNIPAM)-grafted hyaluronan and PNIPAM-grafted gelatin in the control . . . ", Biomaterials, 26(6): 655-659 (2005).

Stile, et al., "Sythesis and Characterization of Injectable Poly(N-isopropylacrylamide)-Based Hydrogels That Support Tissue . . . ", Marcomolecules, 32:7370-7379 (1999).

Zhu, Peng-Wei, "Particle formation and aggregation-collapse behavior of poly(N-isopropylacrylamide) . . . ", J. of Materials Sci.: Materials in Medicine, 15(5):567-573 (2004).

* cited by examiner

*Primary Examiner*—Margaret G Moore
(74) *Attorney, Agent, or Firm*—Novak Druce + Quigg; J. Rodman Steele, Jr.; Gregory M. Lefkowitz

(57) ABSTRACT

The liquid, polymer-containing coating materials of this invention comprise a polymer of a polymerizable, nitrogen-containing, hydrophilic monomer, which may give thermo-responsive properties, and which is copolymerized with a hydrophobic, polymerizable siloxy-containing monomer, in a solvent system of a volatile hydrophobic (non-polar) liquid that is non-stinging to a user. The material forms a coating or bandage in the form of a film when applied to a surface or the skin of a user.

41 Claims, 2 Drawing Sheets

CONFORMABLE BANDAGE AND COATING MATERIAL

CROSS REFERENCE TO RELATED APPLICATIONS

This application claims the benefit of U.S. Provisional Patent Application Ser. No. 60/742,965, filed on Dec. 7, 2005, entitled "CONFORMABLE BANDAGE AND COATING MATERIAL", the entirety of which is incorporated herein by reference.

STATEMENT REGARDING FEDERALLY SPONSORED RESEARCH OR DEVELOPMENT

Not applicable.

FIELD OF INVENTION

This invention relates generally to liquid adhesive materials that are useful for protecting and repairing surfaces such as biological surfaces, including skin and mucous membranes.

BACKGROUND

Alkylsiloxysiloxane-containing hydrophobic polymers admixed with liquid polydimethylsiloxanes (U.S. Pat. No. 5,103,812 and U.S. Pat. No. 4,987,893) provide non-stinging, non-irritating coating materials that allow body fluid evaporation while protecting the body surface from further contamination and desiccation. In another variation, alkylsiloxysiloxane-containing polymers are admixed with 2,2,4-trimethylpentane to provide similar coating properties (U.S. Pat. No. 6,383,502). These coatings have the common disadvantages of loss of adhesion toward hydrated surfaces and loss of adhesion in higher flexibility areas such as knuckles or knees.

Another category of polymer useful as a liquid adhesive bandage, cycloalkyl methacrylate copolymers, has been found to be soluble in a mixture of liquid polydimethylsiloxanes, 2,2,4-trimethylpentane and isododecane (U.S. Pat. No. 6,358,503).

Cyanoacrylates have also found use as liquid adhesive bandages, particularly butyl and octyl cyanoacrylates (U.S. Pat. No. 6,183,593; U.S. Pat. No. 6,143,805). These materials provide quick film formation and are especially useful for closing thin wounds, such as those created by paper or razor cuts. Wounds that are in high flex areas are not suitable for treatment with cyanoacrylates as they tend to increase scarring, if well adhered, or to delaminate quickly, if not well adhered due to their intrinsic brittleness.

Other commercial liquid adhesive bandages are available that are based on compositions that can cause stinging and further irritation of the skin upon application (e.g., New Skin®—Medtech Laboratories of Cody, Wyo. and Curad® Spray Bandage—Beiersdorf AG, Wilton, Conn.).

There is a need in the art to provide a water-insoluble, conformable coating having adhesion to moist and dry surfaces, adhesion under flex stress, moisture vapor and oxygen transmission properties and other necessary properties for use as a protective coating layer on biological surfaces.

SUMMARY

The present invention provides a liquid, amphiphilic polymer-containing coating material that can act as a bandage or dressing to protect or repair wounds or treat damaged or threatened skin or mucosal tissue, when applied in liquid form and air dried on the biological surface to form an adherent, water-insoluble, water-vapor permeable, oxygen permeable, solid protective film without significant stinging to the skin or mucous membranes of the user. The liquid adhesive materials are useful for protecting and repairing surfaces such as biological surfaces, including skin and mucous membranes. The polymer-containing coating materials of this invention support human cell attachment and cell growth. The polymer-containing coating materials of this invention, it is postulated, encourage wound healing by supporting human cell attachment and growth, by providing wound protection, by providing control of water loss and by having high oxygen permeability.

The polymer component of the liquid adhesive material comprises an unsaturated, addition polymerizable, hydrophilic amide, imide, lactam or amine monomer and a hydrophobic, unsaturated, addition polymerizable siloxy-containing monomer. The hydrophilic monomers are all nitrogen-containing, while the hydrophobic siloxy monomers all contain silicon-oxygen groups. The hydrophilic, nitrogen-containing monomers are water soluble, while the hydrophobic siloxy monomers are water insoluble. Because of the dual nature of the monomeric groups, i.e. hydrophilic and hydrophobic, the polymer is amphiphilic. The polymer may also include other monomers. The polymer is dissolved in or compatible with a volatile, hydrophobic solvent, preferably a linear or cyclic siloxane. The ratio of the two monomers is adjusted to render the coating insoluble in water.

The water-insoluble polymer component of the liquid adhesive material may further comprise an addition polymerizable, hydrophilic monomer, whose homopolymer may give thermoresponsive properties when solubilized in an aqueous system or when it is copolymerized with an addition polymerizable siloxysiloxane monomer and added to a solvent system of a volatile, hydrophobic (non-polar) liquid that is non-stinging to a user and said copolymer is placed in an aqueous environment.

The amphiphilic polymer coatings of this invention are insoluble in water, but the coatings allow for water vapor transmission and oxygen permeability. Siloxy-containing polymers are noted for their water vapor permeability and their gas permeability. Such polymers have been used in contact lens materials because of their high oxygen permeabilities. Preferably the polymer is present from about 0.5% up to 70% by weight, more preferably, the polymer is present from about 1% to about 50% by weight, and the volatile hydrophobic liquid from about 30% up to 99.5% by weight, more preferably, from about 50% to 99% by weight. The material forms a water-insoluble coating or bandage in the form of a film when applied to a surface or the skin of a user.

In contrast to the alkylsiloxysiloxane-containing hydrophobic polymers admixed with liquid polydimethylsiloxanes as described in U.S. Pat. No. 5,103,812 and U.S. Pat. No. 4,987,893, where concentrations of polymer in the hydrophobic, volatile linear siloxane could not go above 40% by weight because of insolubility and high viscosity, the present invention utilizing an amphiphilic polymer in the same solvent system allows for polymer concentrations up to 70% by weight and with relatively low viscosity. This solubility and low viscosity is thought to be caused by a micellar-type structure being formed by the amphiphilic polymer in the hydrophobic, volatile solvent, wherein the normally insoluble hydrophilic monomer components are covered by the soluble hydrophobic siloxy monomers in the siloxy solvent. Such an effect would enhance solubility and reduce viscosity. For the polymers of U.S. Pat. No. 5,103,812 and U.S. Pat. No. 4,987, 893, however, hydrophilic monomers were excluded, thus not allowing amphiphilic behavior of the resulting polymer, and thus not facilitating a micellar-type behavior in the volatile, hydrophobic solvent.

The amphiphilic character of the polymer coating facilitates its interaction with dry and moist surfaces. For moist surfaces, that is for surfaces that are slightly wet, the hydrophilic, nitrogen-containing component is able to interact with said moist surface by hydrogen bonding, whereas for dry surfaces, the coating is able to interact with a surface by its adhesive character as well as by hydrogen-bonding of the nitrogen-containing component to any hydrophilic, hydrogen-bond accepting group. The amphiphilic behavior of the polymer coating is demonstrated by stationary contact angle, wherein a dry film has a stationary contact angle of approximately 100° when a drop of deionized water is placed on the film surface, while a hydrated, wet film has a stationary contact angle of approximately 70°. This wetting behavior indicates that phase inversion of the polymer surface occurs, depending on the type of environment that the coating encounters.

In a preferred embodiment, the liquid, polymer-containing coating materials of this invention comprise a polymer from a hydrophilic amide, imide, lactam or amine monomer(s) copolymerized with an alkylsiloxysiloxane monomer(s), a complementary agent that is capable of plasticizing the polymer, or plasticizing the polymer and increasing adhesion, or hydrogen bonding or electrostatically bonding with the hydrophilic monomer of the polymer to increase adhesion, or giving the polymer medicant properties or antimicrobial properties, and a solvent system comprising a volatile, hydrophobic (non-polar) liquid that is non-stinging to a user. Preferably, the plasticizer acts as an adhesion promoter. In a preferred embodiment, the polymer is present from about 0.5% up to 70% by weight, more preferably, from about 1% to about 50% by weight, the complementary agent from about 0.1% up to 30% by weight, more preferably from about 0.1% to about 10% by weight, and the volatile hydrophobic liquid from about 30% up to 99.4% by weight, more preferably, from about 40.0% to about 98.9% by weight. The material forms a coating or bandage in the form of a film when applied to a surface or the skin of a user.

In another preferred embodiment, the polymer comprises at least one addition polymerizable amide, imide, lactam or amine monomer and one addition polymerizable alkylsiloxysilane monomer. The volatile, hydrophobic liquid is preferably a low molecular weight linear or cyclic siloxane. Preferably an adhesion promoting plasticizer is included, including a hydrophobic saccharide derivative for plasticization and film forming ability, a hydrophobic glycol derivative for plasticization and antimicrobial properties, or a hydrophobic phenyl-containing polysiloxane for plasticization and reduced tackiness, or the like.

In a preferred embodiment, the polymer comprises at least one monomeric amide and at least one monomeric siloxysilane. A third monomer component may be included also, if desired, such as to increase or decrease modulus, elasticity, flexibility, adhesion, hydrophilicity or hydrophobicity, and the like. The volatile hydrophobic liquid is preferably a low molecular weight volatile linear or cyclic siloxane.

It is a feature of the invention that the liquid materials can act at a range of application temperatures (−20 to 70° C.) when applied to skin, nails or mucous membranes of a user, which surface temperatures average 30-37° C., to form films in seconds, which films are excellent bandages. The water-insoluble coatings produced are conformable, comfortable and can be elastic and flexible.

The water-insoluble coatings of the invention may be thermoresponsive. As used herein a polymer coating is "thermoresponsive" if any property of the coating is dependent on the temperature of the coating. For example, the relationship between the fluid absorbency of a thermoresponsive coating may be inversely proportional to the temperature of the coating. Similarly, the relationship between the planar dimensions, e.g. length and width, of a coating may also be inversely proportional to the temperature of the coating. Because the coating will typically expand as the hydration level increases, the fluid absorbency, or hydration level, of a coating and the planar dimensions of a coating may be proportional to one another.

The initial adhesion of the inventive coatings to a surface may be produced from flow of the hydrophobic siloxy-containing component of the polymer, presumably because of its low surface energy, combined with hydrogen bonding from the hydrophilic component of the polymer. It is believed that adhesion and cohesion of the coating materials is further enhanced by phase separation of the hydrophilic component of the polymer upon exposure to the moist surface in combination with evaporation of the system's solvent. This is particularly relevant when the hydrophilic monomer component is derived from a polymer that is thermoresponsive at or near body temperature. Subsequent exposure to moisture generally increases adhesion of the water-insoluble film to the surface, possibly due to tightening of the film's interaction with a surface caused by clustering of the phase-separated hydrophilic groups.

Neither the liquid, polymer-containing coating materials nor the subsequently-formed films irritate the skin and mucous membrane during application and during use after drying. The bandages are substantially painless and can be easily removed, if desired, substantially without pain. The dried bandages formed have high water vapor and oxygen transmission throughout. The bandages, when applied over surfaces moist with water, or moist with blood or body fluids, form a tough, adherent film. It is believed that the moisture present diffuses through the polymer coating, increasing the adhesion of the coating to the surface.

The liquid composition and/or dried polymer film can have various medicants or other agents incorporated therein for maintaining sterility, for agent release to the underlying surface, and/or to adjust the electronic properties of the film. For example, antibiotics, anti-infective agents, wound healing agents, disinfectants, anti-itching agents, dermatological agents, steroids, anti-smoking agents, birth control agents, electron-transport agents, or similar materials can be incorporated into the coatings.

In another preferred embodiment, the polymer, when incorporated into volatile non-polar liquids, provides for a fast drying, adherent, flexible, breathable, water-insoluble, water vapor permeable, oxygen permeable, non-stinging liquid adhesive coating or bandage.

In another preferred embodiment, the amphiphilic polymer, when incorporated into volatile, non-polar fluids, provides for reduced viscosity and increased polymer concentrations. This is advantageous if thick polymer coatings are needed that flow easily over a surface, a wound or damaged skin, tissue or mucosal surface.

In another preferred embodiment, a coating is provided that reduces pain and inflammation when applied to damaged or irritated skin or tissue.

In another preferred embodiment, a coating is provided that is an appropriate substrate for cell adhesion and migration.

In another preferred embodiment, the liquid adhesive coating contains therapeutic molecules or other active materials which may be gradually released onto targeted areas.

In another preferred embodiment, the coating is adherent to dry surfaces, moist surfaces, and surfaces that have both dry and moist areas.

In another preferred embodiment, a coating is provided that remains adherent to a surface when exposed to external water, soaps, detergents, and most skincare products.

In another preferred embodiment, a coating is provided that remains adherent to a surface when exposed to varying external humidity and temperature.

In another preferred embodiment, a coating is provided that is adherent under flex stress.

In another preferred embodiment, a coating is provided that prevents further microorganism or particulate contamination to skin or mucous membrane wounds or incisions.

In another preferred embodiment, a transparent or translucent covering is provided that does not attract or hold dirt and can remain colorless and clear for wound viewing as well as cosmetic attractiveness.

In another preferred embodiment, a coating is provided which, when applied, controls body fluid loss from an abraded area.

It is a further object of the invention to provide a polymer film in which medicants or other active agents may be incorporated for release into targeted areas. The release of active agents may be at a controlled rate.

It is a further object of this invention to provide a coating that is water vapor permeable.

It is a further object of this invention to provide a coating that is oxygen permeable.

It is a further object of the invention to provide a coating that, after application to a surface, releases from that surface gradually over time without requiring externally applied solvents or other removal methods.

It is a further object of this invention to provide a coating that allows for cell growth.

Other aspects of the invention are described infra.

DETAILED DESCRIPTION

Figure 1:
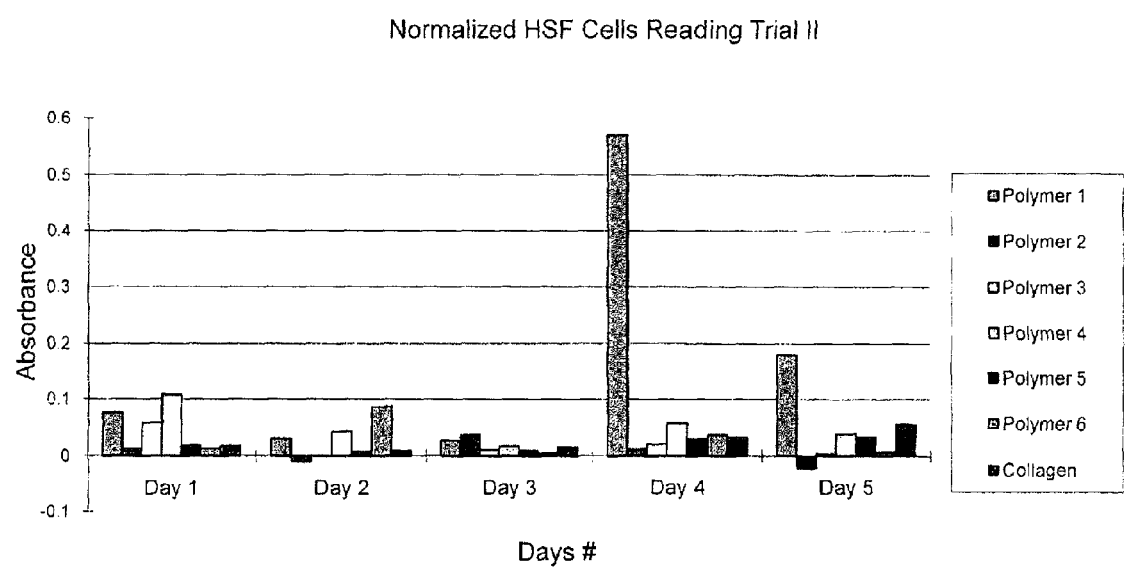
FIG. 1 is a chart of human skin fibroblast absorbency on several polymer formulations.

The amphiphilic polymer of this invention preferably comprises hydrophilic, nitrogen-containing monomers, such as addition polymerizable amides, imides, lactams and or amines, as co-, ter- or multi-components of the polymer copolymerized with hydrophobic alkylsiloxysilane monomers, to generate an amphiphilic polymer that is water insoluble and water vapor permeable when cast from a volatile, hydrophobic solvent.

Typical polymerizable hydrophilic amides, imides, lactams or amines that may be included in the amphiphilic polymer include, but are not limited to:
acrylamide,
N-methylacrylamide,
N-ethylacrylamide,
N-(hydroxymethyl)acrylamide,
N-isopropylacrylamide (NIPAM),
N,N-diethylacrylamide,
N,N-dimethylacrylamide,
N,N-dimethylmethacrylamide,
Diacetone acrylamide,
N-vinylpyrrolidone,
N-vinylcaprolactam,
N-vinylformamide,
N-vinyl-N-methylformamide,
N-vinylacetamide,
2-acetamidoacrylic acid,
2-acrylamidoglycolic acid,
2-acrylamido-2-methyl-1-propanesulfonic acid and its salts,
(3-acrylamidopropyl)trimethylammonium chloride,
4-acryloylmorpholine,
[3-(methacryloylamino)propyl]dimethyl(3-sulfopropyl)ammonium hydroxide inner salt,
[3-(methacryloylamino)propyl]trimethylammonium chloride,
maleimide,
N-methylmaleimide,
N-(2,3-dihydroxypropyl)maleimide,
N-vinylsuccinimide,
N-vinyldiacetamide,
ε-acryloyllysine,
N-acryloyluracil,
N-acryloylthymine,
N-acryloyladenine,
N-acryloylguanine,
N-acryloylurea,
N-acryloylguanidine,
N-acrylglucosamine,
N-allylpyrrolidone,
N-allylacetamide,
N,N-diallylurea,
N,N-dimethylaminoethyl methacrylate,
N,N-dimethylaminoethyl acrylate,
N,N-diethylaminoethyl methacrylate,
N,N-diethylaminoethyl acrylate,
N,N-dimethylaminopropylmethacrylamide,
N,N-dimethylaminopropylacrylamide,
vinylbenzyl-N,N-dimethylamine
methacryloyloxyethylamine,
N-vinylimidazole,
4(5)-vinylimidazole,
4-vinylpyridine,
2-vinylpyridine,
2-methyl-5-vinylpyridine,
vinyltriazine,
4-aminostyrene,
and the like.

Polymerizable hydrophilic amide monomer components useful in the present invention include polymerizable hydrophilic acrylamide-monomers. Typical polymerizable hydrophilic acrylamide-monomers that may be included in the amphiphilic polymer include vinyl-containing amides which can have the following formulas:

$$CH_2=C(R_1)CONR_2R_3$$

Where $R_1=H$, $CH_3$, or $CH_2COOR'$

Where $R'=H$, metal salt, hydroxy alkyl, ethoxyalkyl, $C_1$-$C_{12}$ alkyl, aryl, or fluoralkyl Where $R_2$ and/or $R_3=H$, alkyl ($C_1$-$C_6$), cycloalkyl, amino sugars, amino acids, nucleic acid bases, urea derivatives, alkylammonium salts, alkylsulfonic acids, alkylcarboxylic acids, aryl, alkylaryl, or fluoroalkyl groups. Preferred amides include N-isopropylacrylamide and N,N-dimethylacrylamide.

Preferred polymerizable imides include maleimide and water-soluble derivatives of maleimide, such as N-methylmaleimide and N-(2,3-dihydroxypropyl)maleimide. Additionally, reactive maleimido derivatives can be employed, such as 3-maleimidopropionic acid N-hydroxysuccinimide ester, wherein the coating polymer can be physically bonded to a biological surface through displacement of the hydroxysuccinimide group by a biological nucleophilic group.

Preferred polymerizable lactams include N-vinylpyrrolidone and N-vinylcaprolactam.

Preferred polymerizable amines include N,N-dimethylaminoethyl methacrylate, N,N-dimethylaminopropylacrylamide, and 3- or 4-vinylbenzyl-N,N-dimethylamine.

The amphiphilic polymers may be thermoresponsive in an aqueous environment. Such amphiphilic polymers may be derived from hydrophilic monomers including N-isopropylacrylamide, N-vinylcaprolactam and the like. Such monomers are particularly preferred in this invention as these monomers provide increased adhesion of the coating materials to moist, warm ($\geq 30°$ C.) surfaces, such as skin or mucosal tissue. The increased adhesion may be due to thermoresponsive effects resulting as the coating is heated from room temperature to the higher temperature of the surface to which the coating is adhering. For instance the polymer chain may contract and the hydrogen bonding characteristics of the polymer may increase. The preferred hydrophilic monomer for this thermoresponsive behavior of the coating material is N-isopropylacrylamide.

Polymerizable hydrophobic siloxy-containing monomer components useful in the present invention include polymerizable, hydrophobic siloxysilanes that may be water vapor and oxygen permeable. Polymerizable, hydrophobic siloxysiloxanes that may be reacted with the hydrophilic, nitrogen-containing monomer to form co-polymers, ter-polymers, or multi-polymers include, but are not limited to:
3-methacryloyloxypropyltris(trimethylsiloxy)silane (TRIS),
3-methacryloyloxypropylpentamethyldisiloxane,
3-methacryloyloxypropylbis(trimethylsiloxy)methylsilane,
3-methacryloyloxypropyltris(vinyldimethylsiloxy)silane,
3-methacryloyloxymethylbis(trimethylsiloxy)(pentamethyldisiloxanyl)silane,
3-methacryloyloxyethyltris(pentamethyldisiloxanyl)silane,
methacryloyloxymethylbis(trimethylsiloxy)methylsilane,
methacryloyloxymethyltris(trimethylsiloxy)silane,
3-methacryloyloxypropylheptacyclopentyl-T8-silsesquioxane,
3-methacryloyloxypropylheptaisobutyl-T8-silsesquioxane,
3-acryloyloxypropylmethylbis(trimethylsiloxy)silane,
3-acryloyloxypropyltris(trimethylsiloxy)silane,
3-methacryloyloxypropyl-1,1,1-triphenyl-3,3-dimethyldisiloxane,
methylbis(trimethylsiloxy)silylpropylglyceryl methacrylate,
tris(trimethylsiloxy)silylpropylglyceryl methacrylate,
3-methacrylamidopropyltris(trimethylsiloxy)silane,
3-acrylamidopropyltris(trimethylsiloxy)silane,
p-vinylphenyltris(trimethylsiloxy)silane,
p-vinylbenzyltris(trimethylsiloxy)silane,
vinyloxyethyltris(trimethylsiloxy)silane,
vinylnonyldimethyl(trimethylsiloxy)silane,
vinylnonyltris(trimethylsiloxy)silane,
vinylmethylbis(trimethylsiloxy)silane,
vinylpentamethyldisiloxane,
O-(vinyloxyethyl)-N-(tris[trimethylsiloxy]silylpropyl)urethane,
vinylphenylbis(trimethylsiloxy)silane,
vinyltris(dimethylsiloxy)silane,
vinyltris(trimethylsiloxy)silane,
vinyl-terminated polydimethylsiloxane,
polydimethylsiloxane monoacrylate,
polydimethylsiloxane monomethacrylate,
polymethylphenylsiloxane monoacrylate,
polymethylphenylsiloxane monomethacrylate, and
3-acryloyloxypropyltris(polydimethylsiloxanyl)silane, and the like.

These siloxysilane monomers may provide for solubility in the preferred non-polar, non-stinging solvent systems. Preferred siloxysilane monomers include polymerizable alkyl-siloxysilanes, aryl-siloxysilanes and alkylaryl-siloxysilanes. A preferred polymerizable siloxysilane monomer is 3-methacryloyloxypropyltris(trimethylsiloxy)silane (TRIS).

It should be noted that many siloxysilane monomers may also contain low concentrations of siloxysilane crosslinking agents. These crosslinking agents could be dimeric or higher in their polymerizable groups. For example, the TRIS monomer often contains the dimer of 1,3-bis(3-methacryloyloxypropyl)-1,1,3,3-tetrakis(trimethylsiloxy)disiloxane, which may increase the strength of the coating polymer. Siloxysilane monomer combinations containing siloxysilane monomer crosslinking agents may be utilized in this invention provided that the resulting polymer solubility is not compromised in the volatile, hydrophobic solvent. When the hydrophobic siloxy-containing monomer is TRIS, the dimer content is preferably less than 1.0 wt % of TRIS, more preferably between 0.5-0.8 wt %, and most preferably between 0-0.15 wt %.

Other addition polymerizable monomers may also be incorporated into the polymers of this invention to modify adhesion, cohesion, elasticity, flexibility, toughness, transparency, opaqueness, color, fluorescence, ultraviolet absorbance, increased or decreased refractive index, oxygen permeability, oxygen solubility and combinations thereof. Examples of these other monomers include methyl methacrylate, methyl acrylate, tetrahydrofurfuryl methacrylate, cyclohexyl acrylate, tetrahydrofurfuryl acrylate, n-lauryl acrylate, n-lauryl methacrylate, 2-phenoxyethyl acrylate, 2-phenoxyethyl methacrylate, isodecyl acrylate, isodecyl methacrylate, isooctyl acrylate, isooctyl methacrylate, isobornyl acrylate, isobornyl methacrylate, benzyl acrylate, benzyl methacrylate, 2-butoxyethyl acrylate, n-butyl acrylate, n-butyl methacrylate, ethyl acrylate, ethyl methacrylate, dimethyl itaconate, di-n-butyl itaconate, 2-ethylhexyl acrylate, 2-ethylhexyl methacrylate, furfuryl methacrylate, n-hexyl acrylate, n-hexyl methacrylate, isobutyl acrylate, isobutyl methacrylate, isopropyl methacrylate, pentyl acrylate and methacrylate, 2-pentyl acrylate and methacrylate, 3-pentyl acrylate and methacrylate, 2-methyl-1-butyl acrylate and methacrylate, 1-methyl-1-butyl acrylate and methacrylate, 1-methyl-1-pentyl acrylate and methacrylate, 2-methyl-1-pentyl acrylate and methacrylate, 3-methyl-1-pentyl acrylate and methacrylate, 2-ethyl-1-butyl acrylate and methacrylate, 2-ethyl-1-hexyl acrylate and methacrylate, 3,5,5-trimethyl-1-hexyl acrylate and methacrylate, 3-heptyl acrylate and methacrylate, decyl acrylate and methacrylate, dodecyl acrylate and methacrylate, alpha-methyl styrene, p-t-butyl styrene, 4-methoxystyrene, n-octadecyl acrylate, n-octadecyl methacrylate, 2-phenylethyl acrylate, 2-phenylethyl methacrylate, n-tridecyl methacrylate, vinyl benzoate, vinyl naphthalene and the like. In addition, fluorinated siloxanes, fluorinated itaconates, fluorinated methacrylates or acrylates, such as hexafluoroisopropyl methacrylate, can also be used. Furthermore, dienes such as butadiene or isoprene and their oligomers, derivatized or not, can be used. It is also possible to add a mucoadhesive, hydrophilic monomer such as acrylic or methacrylic acid in quantities of less than 10 mol % of the hydrophilic amide, imide, lactam or amine monomer(s) present in the amphiphilic polymer.

Because of the amphiphilic nature of the monomer mix, any hydrophobic or hydrophilic polymerizable monomer can be used as long as the resulting copolymer exhibits the desired oxygen and water vapor permeability, the desired adhesion and desired cohesion to its applied surface, and maintains water insolubility of the resulting coating. Amphiphilic copolymers of TRIS and acrylamide have been reported (see Polymer, 2004, vol. 45, #2, pp. 337-344), but the resulting polymers did not exhibit the desired properties set forth above.

The polymers of this invention may include between about 15-85 mole percent hydrophilic, nitrogen-containing amide, imide, lactam monomer or amine monomer(s), which component provides coating adhesion onto hydrated and non-hydrated surfaces. A range of about 30-70 mole percent of the hydrophilic monomer in the polymer is preferred in the polymer of this invention. Hydrophobic siloxysiloxane addition polymerizable monomers may make up between about 15-85 mole percent of the polymer composition. These proportions of hydrophilic and hydrophobic monomer components maintains the desired moisture and oxygen permeability and the desired compatibility of the polymer in the volatile liquid hydrophobic liquid. The range of hydrophilic and hydrophobic monomer component percentages allows for adjustment of film characteristics including, but not limited to adhesion, toughness, elasticity, temperature responsiveness, water insolubility, and impact resistance. The preferred nitrogen-containing monomer is N-isopropylacrylamide (NIPAM) and the preferred siloxy-containing monomer is 3-methacryloyloxypropyltris(trimethylsiloxy)silane (TRIS).

Other hydrophobic monomers may be present in the polymer in any amount up to about 30 mole percent. Other hydrophilic monomers may be present in amounts less than about 10 mole percent.

As long, as they are soluble in the volatile, hydrophobic solvent, the amphiphilic polymers may be linear, branched, or slightly crosslinked, and may be co-polymers, ter-polymers or multi-polymers. The amphiphilic polymers may be random copolymers or segmental in nature, such as block copolymers. The polymeric structure may also be stars, branched and hyperbranched polymers, grafts or dendrimers. The amphiphilic polymers may be prepared by free radical polymerization using free radical initiators or photoinitiators. Block copolymers can be prepared by living free radical techniques or, in certain instances, by living ionic techniques.

The vinyl-containing amide component may be thermoresponsive, thus enabling phase separation of the vinyl-containing amide component of the polymer upon exposure to a hydrated surface above the lower critical solution temperature (LCST) of the amide component. This phase separation provides enhanced adhesion to the applied surface and enhanced cohesion of the dried polymer film. For example, polymers of N-isopropylacrylamide have a LCST of between 32 and 35° C. in water, which makes this monomer an excellent candidate, in polymeric form, to release water, aggregate, and form domains when applied to the human skin or mucosal tissue. This aggregation contributes to the void volume in the polymer film, hence increasing oxygen and water vapor permeability, as well as providing enhanced cohesion of the polymer films.

Preferably, the polymers of the invention are addition polymerizable copolymers having a monomer component that is a hydrophilic nitrogen-containing derivative and a monomer component that is a hydrophobic siloxysiloxane derivative.

The preferred hydrophilic, nitrogen-containing monomers are N-isopropylacrylamide and N-vinylpyrrolidone, with N-isopropylacrylamide (NIPAM) being most preferred. The preferred hydrophobic siloxysiloxane monomer is 3-methacryloyloxypropyltris(trimethylsiloxy)silane (TRIS).

Optionally, a third monomer can be included with the hydrophilic, nitrogen-containing monomer and the hydrophobic siloxysilane monomer. The third monomer may be a hydrophobic monomer component that yields a more durable film when cast on a surface, a hydrophilic monomer that has mucoadhesive properties, or both. Such durable, hydrophobic monomers include benzyl methacrylate and 2-phenyl acrylate, and the mucoadhesive, hydrophilic monomers include methacrylic acid and acrylic acid.

Additionally, and preferentially, an adhesion promoter can be added to the coating polymer mixed with the volatile solvent. Adhesion promoters generally function by increasing creep (flow) and tack (stickiness) of a polymer system. Preferably the coatings of the present invention exhibit low tackiness.

Surprisingly, it has been found that plasticizers of hydrophobic, esterified sacharride derivatives, such as sucrose acetate isobutyrate (SAIB), a food additive, and low molecular weight fluid polymers of phenyl-containing polysiloxanes (Dow Corning® 556 Cosmetic Grade Fluid, phenyltrimethicone), increase toughness and adhesion without increasing tack. Further, 2-ethylhexylglycerine, also called octoxyglycerin (Sensiva® SC 50 by Schüilke & Mayr, Rockaway, N.J.) additionally contributes to plasticization and adhesion, but also functions as an antimicrobial agent (see U.S. Pat. No. 6,846,846). Preferably, a composition is formed of 10% by weight of polymer containing a 3/1 ratio by weight of TRIS/NIPAM, with 0.6% by weight of SAIB or 2% by weight of Dow Corning 556®, with the remainder being a volatile solvent, preferably hexamethyldisiloxane, or HMDS. The most preferred formulation for increasing adhesion includes Dow Corning® 556.

If antimicrobial properties are desired for the polymer coating, agents such as silver and silver salts and biguanides such as chlorhexidine, alexidine, or poly(hexamethylene biguanide) can be added to the coating polymer in the volatile solvent, as well as topical antibiotics such as neomycin, polymyxin B, and bacitracin. After evaporation of the volatile, hydrophobic solvent, the polymer coating will contain entrapped antimicrobial agent or antibiotic agent for release to a biological surface.

Once polymerized, vinyl alkylsiloxysiloxane monomers provide the desired polymer compatibility in the volatile hydrophobic liquid, and provide high moisture vapor and oxygen permeability. Vinyl alkylsiloxysilane monomers that may be useful in the present invention may have the following formulas:

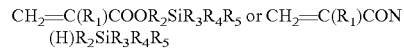

Where $R_1$=H, $CH_3$, or $CH_2COOR'$,
Where $R_2$=H, alkylene ($C_1$-$C_4$) or —$CH_2CH(OH)CH_2$—, —($CH_2CH_2OCH_2CH_2$—)$_x$ where x=1-10, or arylene, or combinations thereof,
Where $R_3R_4R_5$=$OSi(Y)_3$, or alkyl($C_1$-$C_6$),
Where Y=alkyl ($C_1$-$C_6$), or $OSi(Z)_3$,
Where Z=alkyl ($C_1$-$C_6$), aryl, and
Where $R'$=$R_2SiR_3R_4R_5$ Other polymerizable third monomer components may include any hydrophobic acrylate, such as isooctyl acrylate; methacrylate, such as n-butyl methacrylate, benzyl methacrylate and 2-phenylethyl methacrylate; acrylamide, such as N-octylacrylamide; diester of an unsaturated dicarboxylic acid, such as diethyl itaconate and diethyl fumarate; vinyl nitrile, such as acrylonitrile and methacrylonitrile; vinyl ester such as vinyl acetate, vinyl propionate and vinyl laurate; vinyl ether such as butoxyethylene, propoxyethylene and octyloxyethylene; vinyl halide; diene such as butadiene and isoprene; and monomers containing an aromatic ring such as styrene, alpha-methyl styrene and vinyl toluene. A preferred third monomer is benzyl methacrylate. A key contribution of this third hydrophobic monomer is to impart improved durability, a particularly desired feature that enables the coating to adhere to the surface for an extended time and to provide extended surface protection. Other addition polymerizable components may include hydrophilic mucoadhesive monomers such as acrylic acid or methacrylic acid.

It has been found that inventive amphiphilic polymers that include a third monomer may be particularly advantageous since the mole fraction ratios of the polymer may be adjusted to optimize water insolubility, dry and moist surface adhesion, ductility, moisture vapor transmissibility, and oxygen permeability of the film. Amphiphilic polymers containing higher mole fractions of monomers that are soluble in the non-polar solvent are preferred for thicker coatings as this composition allows for higher concentrations of polymer in solvent.

As a preferred option, the polymer of this invention comprises about 30-70 mole percent of the hydrophilic amide, imide, lactam or amine monomer, about 30-70 mole percent of the alkylsiloxysiloxane monomer, about 0-20 mole percent third hydrophobic monomer or about 0-10 mole percent of a hydrophilic mucoadhesive monomer. In a preferred embodiment the amphiphilic polymer comprises about 35 to 55 mole percent N-isopropylacrylamide, about 45 to 65 mole percent 3-methacryloyloxypropyltris(trimethylsiloxy)silane, and about 0-20 mole percent benzyl methacrylate. One variation in the selection of monomers for the polymer of this invention is using more than one monomer within each monomer category. For example, the polymer could comprise 30% N-isopropylacrylamide, 25% dimethylacrylamide, and 45% 3-methacryloyloxypropyltris(trimethylsiloxy)silane. The first two monomers each satisfy the definition of the nitrogen-containing, hydrophilic monomer component, and together provide the desired quantity of this component.

Any free radical initiator can be used in forming the polymers including azobisisobutyronitrile; 2,2'-azobis(2,4-dimethylpentanenitrile); 2,2'-azobis(2-methylbutanenitrile); potassium persulfate; ammonium persulfate; benzoyl peroxide; 2,5-dimethyl-2,5-bis(2-ethylhexanoylperoxy)hexane; and the like. Photoinitators such as Darocure 1173 could also be used to effect polymerization. The polymerization can be carried out by solution, emulsion, bulk, suspension or living free radical techniques. In particular, living free radical polymerization can be used to tailor-make block copolymers.

The polymers of the invention are incorporated into a solvent system comprising volatile hydrophobic liquids, preferably having a solubility parameter from about 6.0-8.0 (cal/cm)$^{1/2}$. The solvent system can comprise volatile liquid silicones including, but not limited to hexamethyldisiloxane (HMDS), octamethylcyclotetrasiloxane, decamethylcyclopentasiloxane, octamethyltrisiloxanes and the like; volatile alkanes, such as 2,2,4-trimethylpentane(isooctane), octane, neopentane and the like; volatile fluorocarbons, such as pentafluoropropane, perfluoroheptane, perfluoromethylcyclohexane and the like; or liquid or supercritical carbon dioxide. Siloxy-based polymers have shown high solubility in liquid or supercritical carbon dioxide. The preferred solvent system for the coating polymer is hexamethyldisiloxane.

Surprisingly, the inventive amphiphilic polymers, which comprise about 30-70 mole percent hydrophilic monomer, are soluble in hydrophobic solvent systems of this invention. The use of these hydrophobic solvent systems, alone or in combination, as the primary liquid phase of the liquid coating provides for rapid drying and less stickiness, or tack, during drying. Additionally, active agents, e.g., medicants, antibiotics, steroids, antimicrobial agents, anti-infective agents, anti-inflammatory agents, anti-itch agents, cell growth factors, or other active pharmaceutical agents, may be more readily incorporated into the solvent/polymer system with its diverse hydrophilic/hydrophobic composition.

Polymer films of the invention cast from liquids containing good solvents with solubility parameters of between about 8 to 10 (cal/cm)$^{1/2}$ will function, but are generally slow to dry and remain tacky for extended periods. Additionally, polar solvents, such as ethanol, 95% ethanol, isopropanol, N-methylpyrrolidone, propylene glycol or glycerin, can be added to the solvent system to chain extend the polymer or provide incorporation of other substances.

Other substances may be added to the liquid material or formulation for plasticization, improved adhesion, or rheology control, and the like. Typical plasticizer/adhesion promoters include, but are not limited to, dibutylphthalate, acetyl tributyl citrate, sucrose acetate isobutyrate, sucrose benzoate, acetyltriethyl citrate, mineral oil, decamethylcyclopentasiloxane, octamethylcyclotetrasiloxane, phenyl-containing polysiloxanes such as phenyltrimethicone, butyl glycolate, and others. Typical rheology additives that may be added to the liquid material or formulation are fumed silica, bentonite and other clay derivatives, and saturated fatty acids, such as hydrated ricinoleic acid.

Medicants

Medicants may be incorporated into the liquid or solid film bandages for ready or continual release as the invention provides for hydrophilic and hydrophobic liquid adhesive material components that allow incorporation of a variety of polar and non-polar medicants, and which are long lasting and highly permeable. Such medicants may be soluble or insoluble in the solvent system. Examples of useful medicants are fungicides, anti-protozoal agents, antibacterial agents, anti-infective agents, anti-inflammatory agents, antiviral agents, antitumor agents, birth control agents, anti-smoking agents, blood pressure and heart regulators, steroids, tissue-growth promoting agents and many more.

Representative examples of antibiotics that may be included in the coating materials described herein include, but are not limited to, penicillins; cephalosporins such as cefadroxil, cefazolin, cefaclor; aminoglycosides such as gentamycin and tobramycin; sulfonamides such as sulfamethoxazole; and metronidazole. Representative examples of anti-inflammatories include: steroids such as prednisone, prednisolone, hydrocortisone, adrenocorticotropic hormone, and sulfasalazine; and non-steroidal anti-inflammatory drugs ("NSAIDS") such as aspirin, ibuprofen, naproxen, fenoprofen, indomethacin, and phenylbutazone. Representative examples of antiviral agents include acyclovir, ganciclovir, zidovudine. Representative examples of antifungal agents include: nystatin, ketoconazole, griseofulvin, flucytosine, miconazole, clotrimazole. Representative examples of anti-protozoal agents include: pentamidine isethionate, quinine, chloroquine, and mefloquine. Representative examples of anti-infective agents include silver and silver salts, chlorhexidine, alexidine, and poly(hexamethylene biguanide).

Tissue growth-promoting agents may be incorporated into the liquid or amphiphilic polymers of this invention to encourage production of new tissue, adhesion of new tissue, cell migration, angiogenesis, etc. For example, cytokines, such as epidermal growth factor, angiopoietin-1, fibroblast growth factor (bFGF), transforming growth factor (TGF)-alpha, TGF-beta and the like, incorporated into the liquid or solid film bandage of this invention may facilitate the regrowth of wounded areas.

A wide variety of molecules may be utilized within the scope of the present invention including for example Anti-Invasive Factor, retinoic acids and their derivatives, paclitaxel including analogues and derivatives thereof, Suramin, Tissue Inhibitor of Metalloproteinase-1, Tissue Inhibitor of Metalloproteinase-2, Plasminogen Activator Inhibitor-I and Plasminogen Activator Inhibitor-2, and lighter "d group" transition metals. Similarly, a wide variety of polymeric carriers may be utilized, representative examples of which include poly(ethylene-vinyl acetate) (40% crosslinked), poly(D,L-lactic acid) oligomers and polymers, poly(L-lactic acid) oligomers and polymers, poly(glycolic acid), copolymers of lactic acid and glycolic acid, poly(caprolactone), poly(valerolactone), polyanhydrides, copolymers of poly(caprolactone) or poly(lactic acid) with poly(ethylene glycol), and blends thereof. Retinoic acid, as well as derivatives thereof which may also be utilized in the context of the present invention.

Paclitaxel (which should be understood herein to include analogues and derivatives such as, for example, TAXOL™, TAXOTERE™, 10-desacetyl analogues of paclitaxel and 3'N-desbenzoyl-3'N-t-butoxy carbonyl analogues of paclitaxel) is a highly derivatized diterpenoid which has been obtained from the harvested and dried bark of *Taxis brevifolia* (Pacific Yew) and Taxomyces Andreanae and Endophytic Fungus of the Pacific Yew. Generally, paclitaxel acts to stabilize microtubular structures by binding tubulin to form abnormal mitotic spindles.

Suramin is a polysulfonated naphthylurea compound that is typically used as a trypanocidal agent. Briefly, Suramin blocks the specific cell surface binding of various growth factors such as platelet derived growth factor ("PDGF"), epidermal growth factor ("EGF"), transforming growth factor ("TGF-β"), insulin-like growth factor ("IGF-1"), and fibroblast growth factor ("βFGF").

A wide variety of other anti-angiogenic factors may also be utilized within the context of the present invention. Representative examples include Platelet Factor 4; Protamine Sulphate (Clupeine); Sulfated Chitin Derivatives (prepared from queen crab shells); Sulfated Polysaccharide Peptidoglycan Complex (SP-PG) (the function of this compound may be enhanced by the presence of steroids such as estrogen, and tamoxifen citrate); Staurosporine; Modulators of Matrix Metabolism, including for example, proline analogs L-azetidine-2-carboxylic acid (LACA), cis-hydroxyproline, D,L-3, 4-dehydroproline, Thiaproline, α,α-dipyridyl, β-aminopropionitrile fumarate; MDL 27032 (4-propyl-5-(4-pyridinyl)-2 (3H)-oxazolone); Methotrexate; Mitoxantrone; Heparin; Interferons; 2 Macroglobulin-serum; ChIMP-3; Chymostatin; β-Cyclodextrin Tetradecasulfate; Eponemycin; Camptothecin; Fumagillin; Gold Sodium Thiomalate ("GST"); D-Penicillamine ("CDPT"); β-1-anticollagenase-serum; α2-antiplasmin; Bisantrene; Lobenzarit disodium (N-(2)-carboxyphenyl-4-chloroanthronilic acid disodium or "CCA"; Thalidomide; Angostatic steroid; AGM-1470; carboxynaminolmidazole; metalloproteinase inhibitors such as BB94.

The compositions of the present invention may also contain a wide variety of other compounds, including for example: α-adrenergic blocking agents, angiotensin II receptor antagonists and receptor antagonists for histamine, serotonin, endothelin; inhibitors of the sodium/hydrogen antiporter (e.g., amiloride and its derivatives); agents that modulate intracellular $Ca^{2+}$ transport such as L-type (e.g., diltiazem, nifedipine, verapamil) or T-type $Ca^{2+}$ channel blockers (e.g., amiloride), calmodulin antagonists (e.g., $H_7$) and inhibitors of the sodium/calcium antiporter (e.g., amiloride); ap-1 inhibitors (for tyrosine kinases, protein kinase C, myosin light chain kinase, $Ca^{2+}$/calmodulin kinase II, casein kinase II); anti-depressants (e.g. amytriptyline, fluoxetine, LUVOX™ and PAXIL™); cytokine and/or growth factors, as well as their respective receptors, (e.g., the interleukins, α-, β- or γ-IFN, GM-CSF, G-CSF, epidermal growth factor, transforming growth factors alpha and beta, TNF, and antagonists of vascular epithelial growth factor, endothelial growth factor, acidic or basic fibroblast growth factors, and platelet derived growth factor); inhibitors of the IP3 receptor (e.g., heparin); protease and collagenase inhibitors (e.g., TIMPs, discussed above); nitrovasodilators (e.g., isosorbide dinitrate); anti-mitotic agents (e.g., colchicine, anthracyclines and other antibiotics, folate antagonists and other antimetabolites, vinca alkaloids, nitrosoureas, DNA alkylating agents, topoisomerase inhibitors, purine antagonists and analogs, pyrimidine antagonists and analogs, alkyl sulfonates); immunosuppressive agents (e.g., adrenocorticosteroids, cyclosporine); sense or antisense oligonucleotides (e.g., DNA, RNA, nucleic acid analogues (e.g., peptide nucleic acids) or any combinations of these); and inhibitors of transcription factor activity (e.g., lighter d group transition metals).

Other types of active agents which may be desirable to incorporate include perfumes, odorants, plant growth regulators, plant insecticides, UV and IR absorbers, etc.

Other Uses and Advantages

The liquid coating materials of this invention may be useful for protecting or treating skin, nails and mucous membranes, e.g. rashes, skin cuts, abrasions, bed sores, incisions and blisters, poison ivy irritation, mosquito bites, eczema, hives, dry cracked skin, abraded gums and other oral surfaces, hemorrhoids and abraded body areas, inflamed digestive tract, and, other mucosal membrane incisions and wounds. The coating material is particularly useful on dry and moist surfaces; and particularly useful on surface areas exposed to high levels of movement, e.g., knuckles, knees, elbows and the like.

Because the liquid bandage is non-stinging and instantly covers exposed nerve endings, pain is reduced immediately. The bandage remains adherent to the skin/mucosal surface for up to about 10 days, relieving pain and gradually lifting off without creating damage or further irritation. For damaged skin and mucosal surfaces, healing appears to occur more quickly compared to the absence of the liquid bandage. This may be due to the enhanced oxygen permeability of the film and its ability to transmit water vapor, as well as its ability to prevent microbial contamination.

Because the coating materials of the present invention may be elastic, they may provide improved adhesion in higher flexibility areas such as knuckles, knees, fingers, toes, etc. In some embodiments of the present invention, the coating materials may be capable of elongating 50% or more without breaking. In a preferred embodiment, the coating materials may be capable of elongating 100% or more without breaking. In an even more preferred embodiment, the coating materials may be capable of elongating 200% or more without breaking.

Normal unabraded skin loses moisture vapor at an average rate of 200 g/m²/day in most areas; the palms of the hand and soles of the feet respire at an average of 500 g/m²/day. The liquid adhesive materials of this invention have moisture vapor transmission rates from 100-300 g/m²/day depending on protective film thickness (0.0005-0.010 inches), thus preventing both dehydration of the wounded area and occlusion of body fluids.

Moisture vapor transmission rate (MVTR) was determined by casting a film of the liquid adhesive materials on deionized water, contained in a glass vessel, e.g. a Mason jar or 10 ml Erlenmeyer flask, to form a continuous polymer film upon evaporation of the liquid adhesive materials solvent. Water loss through the film was measured for a period of 4-7 days and the MVTR calculated based on polymer film surface area and water loss per 24 hours. Polymer film thicknesses were also measured and recorded in mils (0.001 inch units).

The liquid coating materials of this invention support the adhesion of at least two cell types, human epidermal keratinocytes and human skin fibroblasts. Based on five day cell culture growth studies, two to twenty times more keratinocytes or fibroblasts adhered to the polymers of this invention as compared to Collagen Type I. It is postulated that the liquid adhesive compositions of this invention may assist in wound healing as the applied compositions perform as substrates for epidermal cells to adhere and migrate across the top surface of wounds. Other internal injuries and surgical sites could benefit from application of the liquid adhesive coatings of this invention to assist in cell adhesion and migration for healing.

In another application, medical devices may be coated using the coating materials of the present invention to provide a better cellular environment for device acceptance by the human body. This result flows from the fact that the coating materials of this invention are non-toxic, support cell adhesion, and contain relatively high levels of oxygen (U.S. Pat. No. 5,103,812; *Macromolecules*, 1999, 32:7370-9).

Medical devices that may be coated with the inventive coating materials include body-adherent medical devices, implantable medical devices and medical devices that are both implantable and body-adherent. Examples of implantable medical devices to which the inventive coating materials may be applied include, but are not limited to, stents, catheters, joint and bone replacements, implanted pumps, and cardiac pacemakers. Examples of body-adherent medical devices to which the inventive coating materials may be applied include, but are not limited to, bandages, patches, and wound dressings, such as hydrogels, hydrocolloids, foams, and alginates. Examples of medical devices that are both implantable and body adherent and to which the inventive coating materials may be applied include, but are not limited to, medical devices used for procedures such as colostomies, ileostomies, Kock ileostomies, enterostomies and jejunostomies.

The liquid adhesive coating of this invention could be used for applications other than medical body care. For instance, the coating could be used as a membrane, or part thereof, and, as such, could contain conductive additives or other additives to enhance the membrane effectiveness. The coating could be used as a catalyst carrier, thermoresponsive or not, such as those discussed in Bergbreiter, David et al., *Angew. Chem. Int. Ed,* 2000, 39, No. 6, pp. 1040-1042. The coating incorporating a mildewcide could be used to protect grout in tile surfaces. The coating could be used as a water vapor permeable film to protect plants and flowers from dehydrating or to protect them from disease. The liquid adhesive material when cast as a film may be used as a platform for sustaining cells. Further, the dried film can be used to prevent fog from forming on surfaces, such as windshield glass or snorkel masks. The dried film can be used as humidity and dew sensors by monitoring water uptake, swelling, or transparency/opacity. Additionally, the liquid adhesive coating is further useful as a sunscreen with the incorporation of UV absorbers. Still other uses include forming films for use in eliminating chapped lips, treating skin and internal body surfaces, and providing protection to skin and other surfaces that may be medicated prior to application.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

The following examples serve to illustrate the invention without limiting it thereby. It will be understood that variations and modifications can be made without departing from the spirit and scope of the invention.

Examples 1-5 demonstrate dopolymerizations of a siloxysilane monomer and an amide monomer, including illustration of thermoresponsive behavior.

Example 1

Preparation of Poly[(3-methacryloyloxypropyltris (trimethylsiloxy)silane-co-N-isopropylacrylamide] Poly(TRIS/NIPAM)—3/1 parts by weight A 25 ml reaction vessel was charged with 18 g ethyl acetate, 1.5 g (0.004 mol) of 3-methacryloyloxypropyltris (trimethylsiloxy)silane (TRIS), 0.5 g (0.004 mol) N-isopropylacrylamide, and 0.039 g. 2,2'-azobis(2-methylbutanenitrile). After nitrogen flushing for 3 minutes, the vessel was closed and placed in an oil bath. The polymerization was run for 6.5 hours at 63-66° C. The polymer in the reaction liquor was precipitated into water, dissolved in acetone, precipitated again into water, filtered and washed repeatedly, and dried at room temperature (20° C.). A film (0.002-0.0026 in. thick) of the purified polymer cast from hexamethyldisiloxane (HMDS) produced a moisture vapor transmission rate (MVTR) of 60 g/m²/24 hrs. Air-dried films of the polymer cast from HMDS absorbed 394% of their weight of saline at 20° C. and 127% of their weight of saline at 30° C., demonstrating thermoresponsive behavior at higher temperature. The polymer could be dissolved in HMDS up to concentrations of 50 wt %. Films cast from 10 wt % polymer in HMDS (10 μl) remained intact on human forearm skin for 3 days.

Example 2

Preparation of Poly(TRIS/NIPAM)—2.5/1 parts by weight

A 25 ml reaction vessel was charged with 18 g ethyl acetate, 1.42 g (0.003 mol) of TRIS, 0.57 g (0.005 mol) NIPAM, and 0.039 g. 2,2'-azobis(2-methylbutanenitrile). After nitrogen flushing for 3 minutes, the vessel was closed and placed in an oil bath. The polymerization was run for 10 hours at 64-71° C. The polymer in the reaction liquor was precipitated into water, dissolved in acetone, precipitated again into water, filtered and washed repeatedly, and dried at room temperature (20° C.). Films cast from 10 wt % polymer in HMDS (10 μl) remained intact on human forearm skin for up to 10 days.

Example 3

Preparation of Poly(TRIS/NIPAM)—1/1 parts by weight

A 25 ml reaction vessel was charged with 18 g ethyl acetate, 1.0 g (0.002 mol) TRIS, 1.0 g (0.009 mol) NIPAM, and 0.039 g. 2,2'-azobis(2-methylbutanenitrile). After nitrogen flushing for 3 minutes, the vessel was closed and placed in an oil bath. The polymerization was run for 6 hours at 70-73° C. The polymer was precipitated into water, dissolved in acetone, precipitated again into water, filtered and washed repeatedly, and dried at room temperature (20° C.). Air-dried films of the polymer cast from ethyl acetate absorbed 1,071% of their weight in saline at 20° C. and 367% of their weight of saline at 30° C., demonstrating the thermoresponsive behavior of a TRIS/NIPAM copolymer.

Example 4

Preparation of Poly(TRIS/NIPAM)—1/3 parts by weight

A 25 ml reaction vessel was charged with 18 g ethyl acetate, 0.5 g (0.001 mol) TRIS, 1.5 g (0.013 mol) NIPAM, and 0.039 g. 2,2'-azobis(2-methylbutanenitrile). After nitrogen flushing for 3 minutes, the vessel was closed and placed in an oil bath. The polymerization was run for 6 hours at 70-73° C. The polymer was precipitated into water, dissolved in acetone, precipitated again into water, filtered and washed repeatedly, and dried at room temperature (20° C.). Air-dried films of the polymer cast from ethyl acetate absorbed 664% of their weight in saline at 20° C. and 501% of their weight of saline at 30° C., further illustrating the thermoresponsive behavior of the TRIS/NIPAM copolymer.

Example 5

Preparation of Poly(TRIS/NIPAM)—1/1 parts by weight

A 25 ml reaction vessel was charged with 18 g HMDS, 1.0 g (0.002 mol) TRIS, 1.0 g (0.009 mol) NIPAM, and 0.039 g. 2,2'-azobis(2-methylbutanenitrile). After nitrogen flushing for 3 minutes, the vessel was closed and placed in an oil bath. The polymerization was run for 17 hours at 71-72° C. The polymer was precipitated into water and dried at room temperature (20° C.). Film cast from HMDS produced a moisture vapor transmission rate of 322 g/m²/24 hr.

Examples 6 and 7 demonstrate copolymerization of a siloxysilane, an amide, and an added hydrophobic monomer.

Example 6

Preparation of Poly(TRIS/NIPAM/tridecyl methacrylate)—3/1/0.2 parts by weight

A 25 ml reaction vessel was charged with 12 g ethyl acetate, 2.85 g (0.007 mol) TRIS, 0.95 g (0.008 mol) NIPAM, 0.21 g (0.0008 mol) tridecyl methacrylate, and 0.078 g. 2,2'-azobis(2-methylbutanenitrile). After nitrogen flushing for 3 minutes, the vessel was closed and placed in an oil bath. The polymerization was run for 17.5 hours at 76° C. The polymer was precipitated into deionized water, dried at room temperature (20° C.), dissolved in acetone and precipitated into deionized water. The purified polymer was heated at 50° C. to remove bound water. Upon mixing the polymer with HMDS and casting a film, the film had an elongation of 10%. Upon addition of 2 wt % sucrose acetate isobutyrate to the polymer (10 wt %) in HMDS, the cast films had an elongation of greater than 250% without an increase in tack.

Example 7

Preparation of Poly(TRIS/NIPAM/methyl methacrylate)—1.4/1/0.2 parts by weight

A 25 ml reaction vessel was charged with 36 g ethyl acetate, 2.15 g (0.005 mol) TRIS, 1.58 g (0.016 mol) methyl methacrylate, 0.32 g (0.003 mol) NIPAM, and 0.078 g. 2,2'-azobis(2-methylbutanenitrile). After nitrogen flushing for 3 minutes, the vessel was closed and placed in an oil bath. The polymerization was run for 18 hours at 61-65° C. The polymer was precipitated into water and dried at room temperature (20° C.). The polymer was soluble in HMDS.

Examples 8-10 demonstrate the polymerization of a siloxysilane and an amide in a hydrophobic solvent, including the addition of an adhesion promoting plasticizer.

Example 8

Preparation of Poly(TRIS/NIPAM) in 2,2,4-trimethylpentane—3/1 parts by weight

A 25 ml reaction vessel was charged with 12 g 2,2,4-trimethylpentane, 3 g (0.007 mol) TRIS, 1 g (0.009 mol) NIPAM, and 0.082 g. 2,2'-azobis(2-methylbutanenitrile). After nitrogen flushing for 3 minutes, the vessel was closed and placed in an oil bath. The polymerization was run for 5 hours at 69-74° C. The polymer was precipitated into water, filtered, dissolved in acetone, precipitated in water and dried at 50° C. The polymer was partially soluble in HMDS at 10 wt % polymer and contained macroscopic gel particles.

Example 9

Polymer of Example 8 with Poly(N-vinylpyrrolidone) (PVP)

The purified polymer of Example 8 was washed with 50° C. water containing 0.6 g pre-dissolved poly(N-vinylpyrrolidone) (PVP), then filtered and dried at 50° C. for several hours. Subsequently, the polymer (10 wt %) with PVP was added to hexamethyldisiloxane, which produced many macroscopic gel particles.

Example 10

Polymer System of Example 9 with Sucrose Acetate Isobutyrate

The polymer (10 wt %) with PVP of Example 9 was added to hexamethyldisiloxane containing 2 wt % sucrose acetate isobutyrate (SAIB). The mixture was bluish with few macroscopic gel particles.

Examples 11-24 demonstrate the copolymerization of a siloxysilane monomer, an amide and a hydrophobic monomer, with or without added adhesion-promoting plasticizer.

Example 11

Preparation of Poly(TRIS/NIPAM/phenylethyl acrylate)—3/1/0.1 parts by weight

A 25 ml reaction vessel was charged with 11.86 g ethyl acetate, 3 g (0.007 mol) TRIS, 1 g (0.009 mol) NIPAM, 0.14 g (0.0008 mol) 2-phenylethyl acrylate and 0.082 g. 2,2'-azobis(2-methylbutanenitrile). After nitrogen flushing for 3 minutes, the vessel was closed and placed in an oil bath. The polymerization was run for 5 hours at 69-74° C. The polymer was precipitated into water, filtered, dissolved in acetone, precipitated in water and dried at 50° C. The polymer was compatible with HMDS at 10 wt % polymer in the liquid.

Example 12

Preparation of Poly(TRIS/NIPAM/benzyl methacrylate)—3/1/0.1 parts by weight

A 25 ml reaction vessel was charged with 11.86 g ethyl acetate, 3 g (0.007 mol) TRIS, 1 g (0.009 mol) NIPAM, 0.14 g (0.0008 mol) benzyl methacrylate and 0.082 g. 2,2'-azobis(2-methylbutanenitrile). After nitrogen flushing for 3 minutes, the vessel was closed and placed in an oil bath. The polymerization was run for 6 hours at 70-78° C. The polymer was precipitated into water, filtered, dissolved in acetone, precipitated in water and dried at 50° C. The polymer was compatible with HMDS at 10 wt % polymer in the liquid with the presence of macroscopic gel particles.

Examples 13-14

Comparison of Polymer from Example 12 with and without Sucrose Acetate Isobutyrate (SAIB)

The polymer of Example 12 was prepared as 10 wt % in HMDS with (Example 14) and without (Example 13) 2 wt % sucrose acetate isobutyrate (SAIB). 50 µl of each preparation was pipetted onto five replicate glass slides and allowed to dry.

During drying, microscopic observations were made. The polymer in HMDS developed discreet microscopic domains beginning about after 2 minutes of drying and continued to increase in number until 20 minutes of drying. No further changes in domain quantity or size were observed over a 3 day period. The polymer in HMDS with SAIB, when cast on glass, produced small microscopic domains immediately and after 35 minutes the dried films were cloudy to the eye. No further changes in domain quantity or size were observed over a 3 day period. The domains that formed upon drying of the polymer film containing SAIB were more uniform in size than those formed in the polymer film without SAIB.

After 3 days of air drying the polymeric film, coated glass slides were placed in a saline bath at room temperature (about 20° C.) to determine saline absorbance of the films with and without SAIB. The results, which are an average of five replicates, are shown below. It is noted that while saline adsorption did occur, the films remained insoluble in saline solution.

| Average Saline Uptake of poly(TRIS/N-isopropylacrylamide/benzyl methacrylate) | | | | |
|---|---|---|---|---|
| | 2 minutes | 10 minutes | 2 hours | 48 hours |
| Polymer (Ex 13) | 191% | 285% | 280% | 276% |
| Polymer w/SAIB (Ex 14) | 566% | 159% | 256% | 343% |

Examples 15-24

Preparation and Comparisons of Poly(TRIS/NIPAM/benzyl methacrylate)

The polymers of Examples 15-24 were made by free radical polymerization in ethyl acetate at 25% monomer solids using 2,2'-azobis(2-methylbutanenitrile) initiator and holding the reaction solution at 67.5-72° C. for 18.5 hours. The monomers used were 3-methacryloyloxypropyltris(trimethylsiloxy)silane (TRIS), N-isopropylacrylamide (NIPAM), and benzyl methacrylate (BMA). Polymer product was purified by precipitation in room temperature deionized water to remove unreacted monomer and oligomers, filtered, dissolved in acetone, re-precipitated in room temperature water, filtered, washed with 50° C. water, and dried at 50° C. for about 6 hours.

To prepare the test solutions, the dried solid polymer was dissolved in HMDS to make a 10% solids solution. SAIB was added at 2 wt % of total solution. Microscopic observation of domains was determined after drying for approximately 20 minutes.

Tack was determined by rubbing an index finger lightly over dried polymer film on glass slide and rating on a scale from 0 to 5. (0=slippery, 1=smooth, 2=smooth with slight resistance, 3=resistance, 4=resistance with slight stickiness, 5=sticky).

Adhesion to skin was determined by pipetting 10 µl of polymer solution on a human forearm, which previously had been coated with blue food dye. Appearance of the blue dye determined length of polymer adhesion in days. All of the tested films adhered for at least 4 days. Elongation testing was performed by pipetting 3 µl of each polymer solution on a 1 cm length of an 18 cm×0.5 cm rubber band. After drying for 15 minutes the rubber band is stretched manually. The point of polymer breakage is noted as the maximum stretch length.

| Example # | Composition % Monomer ratios TRIS/NIPAM/BMA | Domains in film | Tack | Adhesion to skin (days) | Elongation (%) |
|---|---|---|---|---|---|
| 15 | 45 mol/55 mol/0 | non-uniform clusters | 2 | <7 | 35 |
| 16 | #15 with SAIB | more uniform | 2 | 10 | >200 |
| 17 | 44/55/1 | polygonal | 2 | <7 | 37 |
| 18 | #17 with SAIB | more domains than Ex. 18 | 2 | 10 | >200 |
| 19 | 43/53/4 | very small | 1 | <7 | 35 |
| 20 | #19 with SAIB | few domains | 1 | 10 | >200 |
| 21 | 41/50/9 | very small | 1 | <7 | 35 |
| 22 | #21 with SAIB | many, tiny | 2 | 10 | >200 |
| 23 | 37/46/17 | many, small | 2 | 7 | 30 |
| 24 | #23 with SAIB | many, tiny | 1 | 10 | >200 |

Example 25 demonstrates the copolymerization of a siloxysilane monomer with an amino monomer.

Example 25

Preparation of Poly(TRIS/N,N-dimethylaminoethyl methacrylate)—3/1 parts by weight A 25 ml reaction vessel was charged with 6.0 g ethyl acetate, 1.5 g (0.004 mol) TRIS, 0.5 g (0.006 mol) N,N-dimethylaminoethyl methacrylate (DMAEMA) and 0.078 g. 2,2'-azobis(2-methylbutanenitrile). After nitrogen flushing for 3 minutes, the vessel was closed and placed in an oil bath. The polymerization was run for 16 hours at 66-76° C. The polymer was precipitated into water, filtered, dissolved in acetone, precipitated in water and dried at 50° C. The polymer was compatible in HMDS at 10 wt % polymer in the liquid. When cast on glass the dried clear film had a moderate number of domains of two sizes—less than 0.05 mm and about 0.1 mm. When cast on human forearm the film is non-tacky and fully adherent for 3 days and continued to provide partial coverage for more than 6 days.

Example 26 demonstrates the copolymerization of a siloxysilane monomer with a lactam monomer.

Example 26

Preparation of Poly(TRIS/N-vinylpyrrolidone)—3/1 parts by weight

A 25 ml reaction vessel was charged with 12.0 g ethyl acetate, 3 g (0.007 mol) TRIS, 1 g (0.009 mol) N-vinylpyrrolidone (NVP) and 0.041 g. 2,2'-azobis(2-methylbutanenitrile). After nitrogen flushing for 3 minutes, the vessel was closed and placed in an oil bath. The polymerization was run for 17 hours at 68-72° C. The polymer was precipitated into water, filtered, dissolved in acetone, precipitated in water and dried at 50° C. The polymer partially dissolved in HMDS at 10 wt % polymer in the liquid to produce a stable suspension. When cast on glass the dried opaque film had many domains less than 0.01 mm in size. When cast on human forearm the film is non-tacky and adherent for more than 6 days.

Examples 27-31 demonstrate additional copolymerizations of a siloxysilane with an amine, a lactam, and an amide, with and without plasticizing agents.

Example 27

Preparation of Poly(TRIS/N,N-dimethylacrylamide)—3/1 parts by weight

A 25 ml reaction vessel was charged with 36.0 g ethyl acetate, 3 g (0.007 mol) TRIS, 1 g (0.010 mol) N,N-dimethylacrylamide (DMA) and 0.08 g. 2,2'-azobis(2-methylbutanenitrile). After nitrogen flushing for 3 minutes, the vessel was closed and placed in an oil bath. The polymerization was run for 20 hours at 62-66° C. The polymer was precipitated into water, filtered, dissolved in acetone, precipitated in water and dried at 20° C. The polymer was soluble in HMDS at 10 wt % polymer in the liquid. When cast on glass the dried clear film had a moderate number of round uniform domains about 0.05 mm in size. When cast on human forearm the film is non-tacky and adherent for more than 6 days.

Examples 28-30

Comparisons of the Polymers of Examples 25-27 with and without Sucrose Acetate Isobutyrate The polymers of Examples 25-27 were dissolved in HMDS at 10 wt % solids. To these solutions 2 wt % sucrose acetate isobutyrate (SAIB) was added. The following results, based on the test methods defined in Examples 15-24, were found.

In addition, to determine domain size and quantity within the dried films, 25 µl of each polymer solution was pipetted onto a clean glass slide. After 30 minutes of drying, the domain sizes were measured with a micrometer using a 30× microscope. The quantity of domains was recorded as very few (VF)=less than 5 domains in the entire dried film, few (F)=6-15 domains, moderate (M)=16-50 domains, and many (Mm)=greater than 50 domains in the entire dried film. It is noted that adhesion still occurred when microscopic domains were observable.

| Ex | Composition | Domains in film [quantity, | size(mm)] | Tack | Adhesion to skin (days) | Elongation (%) |
|---|---|---|---|---|---|---|
| 25 | TRIS/DMAEMA | M | 0.05 | 1 | 6 | >250 |
|  |  | M | 0.1 |  |  |  |
| 26 | TRIS/NVP | Mm | 0.01 | 1 | >8 | >250 |
| 27 | TRIS/DMA | F | 0.01 | 1 | >7 | >250 |
|  |  | M | 0.05 |  |  |  |
|  |  | F | 0.1 |  |  |  |
| 28 | TRIS/DMAEMA SAIB | M | 0.05 | 5 | 8 | >250 |
|  |  | F | 0.1 |  |  |  |
| 29 | TRIS/NVP SAIB | Mm | .01-.05 | 3 | >8 | >250 |
|  |  | M | 0.1-0.2 |  |  |  |
|  |  | M | 0.1-0.2 |  |  |  |
| 30 | TRIS/DMA SAIB | M | 0.05 | 5 | >7 | >250 |
|  |  | F | 0.1 |  |  |  |

Example 31

Duplicate preparation of Poly(TRIS/NIPAM)—3/1 parts by wt

A 25 ml reaction vessel was charged with 16.0 g ethyl acetate, 3 g (0.007 mol) TRIS, 1 g (0.009 mol) NIPAM and 0.08 g. 2,2'-azobis(2-methylbutanenitrile). After nitrogen flushing for 3 minutes, the vessel was closed and placed in an oil bath. The polymerization was run for 17 hours at 68-72° C. The polymer was precipitated into water, filtered, dissolved in acetone, precipitated in water and dried at 20° C. The polymer was compatible in HMDS at 10 wt % polymer in the liquid.

Example 32 further demonstrates the thermoresponsive behavior of a coating from a siloxysilane monomer copolymerized with NIPAM.

Example 32

Poly(TRIS/NIPAM) thermoresponsive characteristic

Poly(TRIS/NIPAM) (10 wt %) from Example 31 and SAIB (2 wt %) were dissolved into HMDS. This formulation was applied to human forearm skin and tested for adhesion as defined in Examples 15-24. Removal of the dried polymer film by acetone was then tested by rubbing the polymer film with a paper towel soaked with acetone. At room temperature conditions (~20° C.), the film was readily removed with 3-4 rubs. However, removal of the polymer film after exposure to warm shower/bath conditions required more than 20 rubs with acetone, hence, demonstrating the poly(TRIS-co-NIPAM) contraction, tighter skin adhesion and water expulsion upon exposure to warmer temperatures Examples 33-37 illustrate the effects of various complementary agents added to a siloxysilane copolymer with NIPAM.

Examples 33-37

Comparison of the Polymer of Example 31 with Added Complementary Agents

Hydrophobic hydrogen-bonding complements were added to the polymer of Example 31, which was dissolved in HMDS at 10 wt % solids. The complements were added at a concentration of 1 wt %. At least three of these complements are known to have medicinal value, namely 2-ethylhexylglycerin, vitamin E and Rifampicin. Polyoxyethylene-20-sorbitan monolaurate is often used as an emulsifier and dispersing agent. Butyloctyl tallowate, a high molecular weight ester adhesion promoter, was obtained from Jarchem Industries Inc., Jarester I-1202. The following results were found. The test techniques are defined in Examples 15-24 and Examples 28-30.

| Ex | Complement | Domains in film [quantity, size(mm)] | | Tack | Adhesion to skin (days) | Elongation (%) | MVTR (g/m$^2$/dy) |
|---|---|---|---|---|---|---|---|
| 31 | none | M | 0.05-0.1 | 2 | 4 | 20 | 132 |
|    |      | VF | 0.3 |   |   |    |     |
| 33 | 2-ethylhexylglycerin | M | 0.05-1 | 3 | 4 | >250 |   |
| 34 | vitamin E | M | 0.05-0.1 | 3 | >7 | 70 |   |
|    |           | F | 0.10-0.15 |   |    |    |   |
| 35 | Rifampicin | Mm | 0.05-0.1 | 2 | — | 20 |   |
|    |            | F | 0.1-0.2 |   |   |    |   |
| 36 | polyoxyethylene-20-sorbitan monolaurate | VF | 0.05-0.1 | 2 | 6 | 10 | 149 |
|    |                                         | M  | 0.1-0.2  |   |   |    |     |
| 37 | butyloctyl tallowate | F | 0.05-0.1 | 2 | 6 | 20 | 144 |
|    |                      | VF | 0.1-0.2 |   |   |    |     |

Example 38 demonstrates a coating in a mixture of volatile, hydrophobic solvents.

Example 38

Polymer of Example 31 Dissolved in Pentafluoropropane

The polymer of Example 31 was mixed at 10 wt % solids into a solvent 50/50 mixture of hexamethyldisiloxane and pentafluoropropane. The resulting solution was transparent which when cast on glass produced a dried polymer film with few small (0.05-0.10 mm) domains (test defined, Examples 28-30). The tack of this dried film was at a level of 2 (test defined, Examples 15-24).

Example 39 demonstrates the copolymerization of a siloxysilane monomer with mixed amide and lactam monomers.

Example 39

Preparation of Poly(TRIS/N-isopropylacrylamide/N-vinylpyrrolidone) (TRIS/NIPAM/NVP) 6/1/1 parts by weight A 25 ml reaction vessel was charged with 12.41 g ethyl acetate, 3.04 g (0.007 mol) TRIS, 0.51 g (0.005 mol) NVP, 0.51 g (0.005 mol) NIPAM and 0.078 g. 2,2'-azobis(2-methylbutanenitrile). After nitrogen flushing for 3 minutes, the vessel was closed and placed in an oil bath. The polymerization was run for 15 hours at 71° C. The polymer was precipitated into water, dried at room temperature (20° C.), dissolved in acetone, precipitated into DI water, and dried at 50° C. to release bound water. The polymer (10 wt %) when mixed with HMDS produced a translucent liquid. This coating when applied to human forearm skin produced a film that adhered for 8 days. A 10 mil thick film of the polymer of this example had a moisture vapor transmission rate of about 180 g/m$^2$/24 hrs.

Example 40 demonstrates the copolymerization of a siloxysilane with a lactam monomer and a hydrophilic, mucoadhesive monomer.

Example 40

Preparation of Poly(TRIS/N-vinylpyrrolidone/methacrylic acid) (TRIS/NVP/MAA)—14/1/1 parts by weight A 25 ml reaction vessel was charged with 12 g ethyl acetate, 3.54 g (0.008 mol) TRIS, 0.26 g (0.002 mol) NVP, 0.21 g (0.002 mol) methacrylic acid (MA) and 0.08 g. 2,2'-azobis(2-methylbutanenitrile). After nitrogen flushing for 3 minutes, the vessel was closed and placed in an oil bath. The polymerization was run for 16 hours at 63-82° C. The polymer was precipitated into water, filtered, dissolved in acetone, precipitated in water and dried at 50° C. resulting in a 58% yield. The polymer was partially soluble in HMDS at 10 wt % polymer in the liquid. When cast on glass the dried film had a moderate number of domains between 0.01 mm and 0.05 mm (test defined, Examples 28-30). A 10 mil thick film of the dried polymer had a moisture vapor transmission rate of 199 g/m$^2$/24 hr. The dried film had an elongation of 87% (test defined, Examples 15-24). When applied to human forearm the dried polymer film adhered for 3 days.

Example 41 demonstrates the copolymerization of a siloxysilane monomer with an imide monomer.

Example 41

Poly(TRIS/maleimide) 6/1 parts by weight

A 50 ml reaction vessel was charged with 12 g ethyl acetate, 1.5 g ethanol (190 proof), 3.44 g (0.008 mol) TRIS, 0.57 g (0.006 mol) maleimide and 0.04 g 2,2'-azobis(2-methylbutanenitrile). After nitrogen flushing for 3 minutes, the heating mantle was turned on. The polymerization was run for 5 hours at 70-74° C. The polymer was precipitated into methanol, filtered, and dried at approximately 37° C., resulting in an 80% yield. The polymer was soluble in HMDS and formed a non-tacky, transparent adherent film on human skin.

Examples 42 and 43 demonstrate the copolymerization of a siloxysilane monomer with an amide monomer, including a hydrophobic fluoromonomer.

Example 42

Preparation of
Poly(Tris/N-isopropylacrylamide/trifluoroethyl
methacrylate) (TRIS/NIPAM/TFEMA—3/1/0.3 parts
by weight A 100 ml reaction vessel was charged with 12.4 g ethyl acetate, 2.84 g (0.007 mol) TRIS, 1.00 g (0.009 mol) NIPAM, 0.30 g (0.002 mol) trifluoroethyl methacrylate (TFEM) and 0.08 g. 2,2'-azobis(2-methylbutanenitrile). After nitrogen flushing for 3 minutes, the vessel was closed and placed in an oil bath. The polymerization was run for 22 hours at 63-74° C. The polymer was precipitated into water, filtered, dissolved in acetone, precipitated in water and dried at 50° C. resulting in an 83% yield. The polymer was soluble in HMDS and formed a flexible film when cast on Teflon sheeting.

Example 43

Preparation of
Poly(TRIS/N-isopropylacrylamide/dodecafluoroheptyl
methacrylate) (TRIS/NIPAM/DFHMA)—3/1/0.7
parts by weight A 25 ml reaction vessel was charged with 15 g ethyl acetate, 3.23 g (0.008 mol) TRIS, 1.09 g (0.010 mol) NIPAM, 0.69 g (0.002 mol) 2,2,3,3,4,4,5,5,6,6,7,7-dodecafluoroheptyl methacrylate (DFHMA) and 0.101 g 2,2'-azobis(2-methylbutanenitrile). After nitrogen flushing for 3 minutes, the vessel was closed and placed in an oil bath. The polymerization was run for 15.5 hours at 63-79° C. The polymer was precipitated into water, filtered, dissolved in acetone, precipitated in water and dried at 50° C. resulting in an 83% yield. The polymer was compatible in HMDS at 10 wt % polymer in the liquid. When cast on glass the dried clear film had a moderate number of domains between 0.02 mm and 0.05 mm in size (test defined, Examples 28-30).

Example 44 demonstrates an additional copolymerization of a siloxysilane monomer and a lactam monomer.

Example 44

Preparation of Poly(TRIS/NVP)—4.5/1 parts by
weight

A 25 ml reaction vessel was charged with 16 g ethyl acetate, 4.91 g (0.012 mol) TRIS, 1.11 g (0.010 mol) N-vinylpyrrolidone (NVP) and 0.12 g. 2,2'-azobis(2-methylbutanenitrile). After nitrogen flushing for 3 minutes, the vessel was closed and placed in an oil bath. The polymerization was run for 15.5 hours at 69° C. The polymer was precipitated into water, filtered, dissolved in acetone, precipitated in water and dried at 50° C. resulting in an 83% yield. The polymer was partially soluble in HMDS at 10 wt % polymer in the liquid. When cast on glass the dried film had many domains between 0.01 mm and 0.02 mm and a few domains between 0.03 and 0.4 mm in size (test defined, Examples 28-30). The dried film had an elongation of greater than 250% (test defined, Examples 15-24). When applied to human forearm the dried polymer film adhered for 5 days.

Examples 45 and 46 demonstrate cell adhesion to siloxysilane copolymers with an amide or lactam monomers.

Example 45

Cell Adhesion Studies

The polymer of Example 31 [poly(TRIS/NIPAM)] was dissolved in HMDS at 10 wt % solids with 2 wt % sucrose acetate isobutyrate. The polymer solution was then evaluated, after application, for the ability of human skin fibroblasts (HSF) and human epidermal keratinocytes (HEK) to adhere to the polymer film. The cell culture media were purchased along with cells from American Type Culture Collection (ATCC) and Cell Applications Inc. respectively. Cells were incubated at 37° C. with 5% $CO_2$. 96-Well plates were filled with 10 µl of Type I Collagen (purchased from Sigma Aldrich) per each well (0.01 mg/ml in 1% acetic acid), and then dried in a closed laminar flow hood overnight (about 24 to 28 hours). 10 µl of the polymer solution of Example 31 was pipetted onto the dried Collagen and air-dried for 2 minutes to allow for evaporation of the hexamethyldisiloxane. Then 150 µl of cell culture media was pipetted onto the polymer. Within each well plate, eight replicates of each cell type were used and the series of tests were performed twice over a period of three weeks. The testing occurred on each day of five-day runs. Using a SRB Assay method (Sulforhodamine B cytoxicity and cell growth assay), the samples in each of the well plates were fixed with 10% formaldehyde (Formal Fixx concentrate purchased from Thermo Shandon) and prepared for cell concentration testing using a GENios Microplate Fluorometer at 520 nm absorbance. Collagen, without polymer solution, was used as the control for cell adhesion. The higher the absorbance reading, the higher the cell concentration.

In all trials the trend was repeated that better cell adhesion was found with poly(TRIS/NIPAM) (of Example 31 as formulated in Example 45) than with Type I Collagen alone. With HEK (keratinocytes) cells, the poly(TRIS/NIPAM) film demonstrated approximately 2 to 10 times improvement in cell adhesion based on absorbance values. With HSF (fibroblasts) cells, the poly(TRIS/NIPAM) film demonstrated approximately 2 to 20 times improvement in cell adhesion based on absorbance values.

| HEK Cell Concentration as measured by Absorbance at 520 nm | | | | | |
|---|---|---|---|---|---|
| Polymer | Day 1 | Day 2 | Day 3 | Day 4 | Day 5 |
| TRIAL ONE | | | | | |
| Collagen | 0.0072 | −0.0010 | −0.0021 | 0.00243 | −0.0008 |
| Poly(TRIS/NIPAM) | 0.02315 | 0.02458 | 0.01081 | 0.0155 | 0.0524 |
| TRIAL TWO | | | | | |
| Collagen | 0.01473 | 0.00719 | 0.0089 | 0.0123 | 0.01165 |
| Poly(TRIS/NIPAM) | 0.04986 | 0.01424 | 0.03975 | 0.02669 | 0.02679 |

| HSF Cell Concentration as measured by Absorbance at 520 nm | | | | | |
|---|---|---|---|---|---|
| Polymer | Day 1 | Day 2 | Day 3 | Day 4 | Day 5 |
| TRIAL ONE | | | | | |
| Collagen | 0.0122 | 0.00478 | 0.0114 | 0.02867 | 0.05176 |
| Poly(TRIS/NIPAM) | 0.07799 | 0.02985 | 0.02615 | 0.5689 | 0.17875 |
| TRIAL TWO | | | | | |
| Collagen | 0.00338 | 0.00094 | 0.00265 | 0.00185 | 0.00476 |
| Poly(TRIS/NIPAM) | 0.04499 | 0.03894 | 0.04884 | 0.04455 | 0.04549 |

Example 46

Cell Adhesion Studies with Perfluorobutylamine

The polymers of Example 31 [poly(TRIS/NIPAM)] and Example 43 [poly(TRIS/NIPAM/DFHMA)] were dissolved in HMDS at 10 wt % solids with 2 wt % sucrose acetate isobutyrate. The polymer of Example 44 [poly(TRIS/NVP)] was dissolved in HMDS at 10 wt % solids. To each of the three formulations, perfluoro-t-butylamine was added to saturation (<1 wt %). Perfluoro-t-butylamine is known to incorporate oxygen; hence, this chemical was added to the formulation to potentially provide more oxygen to proliferating cells. The polymer solutions were evaluated, after application, for the ability of human skin fibroblasts (HSF) and human epidermal keratinocytes (HEK) to adhere to the polymer films according to the procedures of Example 45.

All formulations demonstrated more cell adhesion than Collagen during TRIAL II below, but the results were not duplicated in a subsequent trial except with poly(TRIS/NIPAM), as shown in Example 45 data as well as FIG. 2. Additionally, keratinocytes consistently showed better growth on the dried polymer films than fibroblasts. Accordingly, in one aspect of the present invention, the coating material serves as a healing agent by promoting cell growth.

Figure 2:
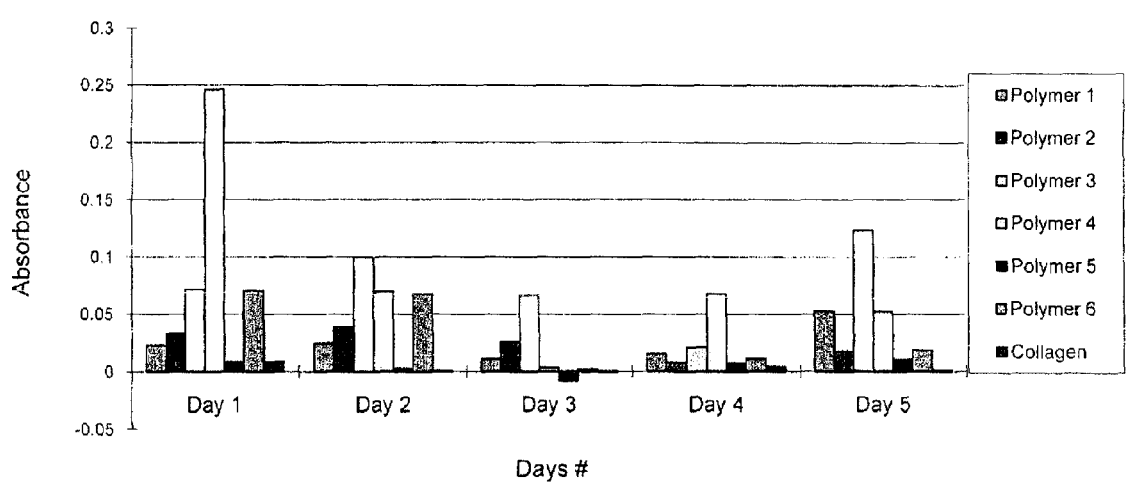
FIG. 2 is a chart of human epidermal keratinocyte absorbency on several polymer formulations.

In FIGS. 1 and 2, Polymer 1=Poly(TRIS/NIPAM) formulation of Example 45, Polymer 2=Poly(TRIS/NIPAM) formulation of Example 46, Polymer 3=Poly(TRIS/NIPAM/DFHMA) formulation of Example 46, Polymer 4=Poly(TRIS/NVP) formulation of Example 46 without perfluoro-t-butylamine, Polymer 5=Poly(TRIS/NVP) formulation of Example 46, and Polymer 6=3M NexCare™ No Sting Liquid Bandage. 3M NexCare™ No Sting Liquid Bandage contains hexamethyldisiloxane, acrylate terpolymer and polyphenylmethylsiloxane. The results indicate perfluoro-t-butylamine acts as a healing agent by promoting cell growth.

Example 47 demonstrates the copolymerization of a siloxysilane monomer with an amide monomer, with added siloxy-containing polymer as a complementary, adhesion-promoting, plasticizing agent.

Example 47

Poly(TRIS/NIPAM) with Dow Corning® 556 Cosmetic Grade Fluid

Dow Corning® 556 Cosmetic Grade Fluid, phenyltrimethicone, a plasticizing agent, was added at 2 wt % to the polymer of Example 31 [poly(TRIS/NIPAM)], which was dissolved at 10 wt % in HMDS. When applied to human forearm skin, the dried polymer film adhered for more than 5 days and had a tack level of 1. The dried polymer film (5 mil thickness) had a moisture vapor transmission rate of 1130 g/m²/24 hr at 37° C. and 342 g/m²/24 hr at 20° C. The dried film exhibited a 233% elongation (tests defined in Examples 15-24).

Example 48 demonstrates the copolymer of a siloxysilane monomer with a lactam monomer containing a complementary, antimicrobial, plasticizing agent.

Example 48

Poly(TRIS/NVP) with antimicrobial agent

A 25 ml reaction vessel was charged with 12 g ethyl acetate, 3.33 g (0.008 mol) TRIS, 0.667 g (0.006 mol) N-vinylpyrrolidone (NVP) and 0.08 g. 2,2'-azobis(2-methylbutanenitrile). After nitrogen flushing for 3 minutes, the vessel was closed and placed in an oil bath. The polymerization was run for 19 hours at 61-71° C. The polymer was precipitated into water, filtered, dissolved in acetone, precipitated in water and dried at 50° C., resulting in a 64% yield. The polymer (10 wt %) and 2-ethylhexylglycerin (Sensiva 50 from Schülke & Mayr) (1.5 wt %) were mixed into HMDS. The resulting formulation was biocidal towards *Staphylococcus aureus*, *Staphylococcus epidermidis*, and *Serratia marcescens*. The formulation without 2-ethylhexylglycerin was not biocidal.

Examples 49-51 demonstrate pain reduction and enhanced skin healing.

Example 49

Skin Tear Injury

A 56-year old Caucasian woman accidentally scrapped skin off the knuckle of her right hand. Over a period of approximately 3 days with treatment using antibiotic ointments, the injury continued to be progressively more inflamed and painful (itching). A formulation composed of 10 wt % Example 31 polymer, 2 wt % phenyltrimethicone (Dow Corning 556) and 88% hexamethyldisiloxane was applied to the skin tear. The resulting dried polymer film was non-tacky, transparent and flexible. The injured area stopped hurting immediately and healed completely in 2 days.

Example 50

Knife Cut

A 55-year old Caucasian woman accidentally cut her finger at the knuckle with a kitchen knife. The cut was sealed with 3M NexCare™ Liquid Bandage (n-butyl cyanoacrylate) and then coated with the formulation of Example 32. The resulting dried polymer film was non-tacky, transparent and flexible. The cut completely healed in 3 days. With previous similar cuts, using treatments such as antibiotic ointments, healing occurred in greater than 10 days.

Example 51

Cold Sore

A 66-year old Caucasian male applied the formulation of Example 32 or the formulation of Example 49 onto cold sores on his lips as they developed over a 6 month period. Upon application of either of the formulations, the itching ceased. The formulations were re-applied daily and provided reduced cold sore size and complete healing within 7 days. This compared to a normal 10 day period for an untreated cold sore to complete its cycle [appearance to completely healed].

The above examples are representative of specific embodiments of the present invention. However, many variations are possible. In all forms, the coating material of this invention contains a polymer comprising a polymerizable, nitrogen-containing, hydrophilic, amide, imide, lactam or amine, and a polymerizable, hydrophobic alkylsiloxysiloxane or alkylarylsiloxysiloxane, and a solvent system comprising a volatile, hydrophobic liquid. In all cases the invention provides a method of forming a coating on a surface by applying a liquid, polymer-containing formulation or material to the surface and volatilizing the non-stinging solvent system to form a coating that is adherent to the surface, which may be moist or dry and/or flexible, and which can protect the surface from external insults.

Other Embodiments

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

What is claimed is:

1. A liquid, polymer-containing coating material comprising about 1 to 50 wt % amphiphilic polymer and about 50 to 99 wt % of a non-stinging, volatile, hydrophobic liquid as part of a solvent system, said amphiphilic polymer being dissolved in said solvent system; wherein the weight percentages are based on the total weight of the liquid, polymer-containing coating material; wherein said amphiphilic polymer comprises at least one polymerizable nitrogen-containing monomer component whose homopolymer is soluble in water and at least one polymerizable siloxy-containing monomer component that is hydrophobic; wherein said liquid coating material forms an adherent, conformable, water-vapor permeable, water-insoluble coating when applied to a surface, wherein the amphiphilic polymer comprises about 15 to 85 mole % polymerizable nitrogen-containing monomer component and about 15 to 85 mole % polymerizable siloxy-containing monomer component; and wherein said non-stinging, volatile, hydrophobic liquid is a non-stinging, volatile, hydrophobic liquid selected from the group consisting of volatile linear and cyclic siloxanes, volatile alkanes, volatile fluorocarbons, liquid and supercritical carbon dioxide, and mixtures thereof.

2. The liquid, polymer-containing coating material in accordance with claim 1, wherein said hydrophilic polymerizable nitrogen-containing monomer component is selected from the group consisting of polymerizable amides, imides, lactams and amines.

3. The liquid, polymer-containing coating material according to claim 2, wherein said hydrophilic polymerizable nitrogen-containing monomer component is selected from N-isopropylacrylamide, N,N-dimethylacrylamide, N,N-dimethylaminoethyl methacrylate, maleimide and N-vinylpyrrolidone.

4. The liquid, polymer-containing coating material according to claim 1, wherein said hydrophobic polymerizable siloxy-containing monomer component is selected from the group consisting of polymerizable alkyl-siloxysilanes, alkylaryl-siloxysilanes, or aryl-siloxysilanes.

5. The liquid, polymer-containing coating material according to claim 4, wherein said hydrophobic polymerizable siloxy-containing monomer component is 3-methacryloyloxypropyltris(trimethylsiloxy)silane.

6. The liquid, polymer-containing coating material according to claim 1, wherein said hydrophilic polymerizable nitrogen-containing monomer component is N-isopropylacrylamide and said hydrophobic polymerizable siloxy-containing monomer component is 3-methacryloyloxypropyltris(trimethylsiloxy)silane.

7. The liquid, polymer-containing coating material according to claim 1, wherein said non-stinging, volatile hydrophobic liquid is hexamethyldisiloxane.

8. The liquid, polymer-containing coating material according to claim 1, wherein said amphiphilic polymer further comprises a third polymerizable monomer component.

9. The liquid, polymer-containing coating material according to claim 8, wherein said amphiphilic polymer further comprises about 0.1 to 20 mole % polymerizable third monomer component.

10. The liquid, polymer-containing coating material according to claim 9, wherein said polymerizable third monomer component is a selected from the group consisting of benzyl methacrylate, 2-phenyl acrylate, methacrylic acid, acrylic acid, and combinations thereof.

11. The liquid, polymer-containing coating material according to claim 9, wherein the polymerizable nitrogen-containing monomer is N-isopropylacrylamide, the polymerizable siloxy-containing monomer is 3-methacryloyloxypropyltris(trimethylsiloxy)silane, and the polymerizable third monomer component is benzyl methacrylate.

12. The liquid, polymer-containing coating material according to claim 1, further comprising 0.1 to 10 wt % complementary agent, wherein said complementary agent is selected from the group consisting of a plasticizer, an adhesion promoter, an antimicrobial agent, a healing agent, a medicant, and combinations thereof.

13. The liquid, polymer-containing coating material according to claim 12, wherein said complementary agent comprises a plasticizer selected from the group consisting of a hydrophobic saccharide derivative, a hydrophobic glycol derivative, a hydrophobic phenyl-containing polysiloxane, 2-ethylhexylglycerin, dibutylphthalate, acetyl tributyl citrate, sucrose acetate isobutyrate, sucrose benzoate, acetyltriethyl citrate, mineral oil, decamethylcyclopentasiloxane, octamethylcyclotetrasiloxane, phenyl-containing polysiloxanes, and combinations thereof.

14. The liquid, polymer-containing coating material according to claim 12, wherein said complementary agent comprises an adhesion promoter selected from the group consisting of butyloctyl tallowate, 2-ethylhexylglycerin, a hydrophobic saccharide derivative, dibutylphthalate, acetyl tributyl citrate, sucrose acetate isobutyrate, sucrose benzoate, acetyltriethyl citrate, mineral oil, decamethylcyclopentasiloxane, octamethylcyclotetrasiloxane, a phenyl-containing polysiloxane, and combinations thereof.

15. The liquid, polymer-containing coating material according to claim 12, wherein said complementary agent comprises an antimicrobial agent selected from the group consisting of a hydrophobic glycol derivative, 2-ethylhexylglycerin, silver, silver salts, biguanides, neomycin, polymyxin B, bacitracin, and combinations thereof.

16. The liquid, polymer-containing coating material according to claim 12, wherein said complementary agent comprises a medicant selected from the group consisting of an antibiotic, an anti-infective agent, an antiviral agent, a wound healing agent, a disinfectant, an anti-itching agent, a dermatological agent, a steroid, an anti-smoking agent, a birth control agent, an electron-transport agent, and combinations thereof.

17. The liquid, polymer-containing coating material according to claim 12, wherein said complementary agent comprises an antimicrobial agent, a medicant, or both; wherein said antimicrobial agent, medicant, or both, contained in said adherent, conformable, water-vapor permeable coating are released to the surface.

18. The liquid, polymer-containing coating material according to claim 17, wherein said antimicrobial agent, medicant, or both, are released to the surface at a controlled rate.

19. The liquid, polymer-containing coating material according to claim 12, wherein said complementary agent is selected from the group consisting of hydrophobic saccharide derivatives, hydrophobic phenyl-containing polysiloxanes, and combinations thereof.

20. The liquid, polymer-containing coating material according to claim 19, wherein the complementary agent is selected from the group consisting of sucrose acetate isobutyrate, phenyltrimethicone, and combinations thereof.

21. The liquid, polymer-containing coating material according to claim 1, wherein said adherent, conformable, water-vapor permeable coating is thermoresponsive.

22. The liquid, polymer-containing coating material according to claim 1, wherein said adherent, conformable, water-vapor permeable coating encourages cell adhesion.

23. The liquid, polymer-containing coating material according to claim 22, wherein said liquid, polymer-containing coating material further comprises perfluoro-t-butylamine.

24. The liquid, polymer-containing coating material according to claim 22, wherein said surface is damaged skin and said adherent, conformable, water-vapor permeable coating encourages healing.

25. The liquid, polymer-containing coating material according to claim 1, wherein said surface is a surface of a medical device and said medical device is an implantable medical device, a body-adherent medical device, or a medical device that is both implantable and body-adherent.

26. A method of forming an adherent, conformable, water-vapor permeable coating on a surface, comprising the steps of:
applying the liquid, polymer-containing coating material of claim 1 to a surface; and
evaporating said volatile, hydrophobic liquid to form an adherent, conformable, water-vapor permeable coating.

27. The method of forming an adherent, conformable, water-vapor permeable coating on a surface according to claim 26, wherein the hydrophilic polymerizable nitrogen-containing monomer component is selected from the group consisting of amides, imides, lactams, amines, and combinations thereof.

28. The method of forming an adherent, conformable, water-vapor permeable coating on a surface according to claim 26, wherein the hydrophilic polymerizable nitrogen-containing monomer component is N-isopropylacrylamide, the hydrophobic polymerizable siloxy-containing monomer component is 3-methacryloyloxypropyltris(trimethylsiloxy) silane, and the volatile, hydrophilic liquid is hexamethyldisiloxane.

29. The method of forming an adherent, conformable, water-vapor permeable coating on a surface according to claim 26, wherein said liquid, polymer-containing coating material further comprises a phenyl-containing polysiloxane, sucrose acetate isobutyrate, or both.

30. The method of forming an adherent, conformable, water-vapor permeable coating on a surface according to claim 26, wherein said adherent, conformable, water-vapor permeable coating is thermoresponsive.

31. The method of forming an adherent, conformable, water-vapor permeable coating on a surface according to claim 26, wherein said adherent, conformable, water-vapor permeable coating encourages cell adhesion.

32. The method of forming an adherent, conformable, water-vapor permeable coating on a surface according to claim 31, wherein said liquid, polymer-containing coating material further comprises perfluoro-t-butylamine.

33. The method of forming an adherent, conformable, water-vapor permeable coating on a surface according to claim 31, wherein said surface is damaged skin and said adherent, conformable, water-vapor permeable coating encourages healing.

34. The method of forming an adherent, conformable, water-vapor permeable coating on a surface according to claim 26, wherein said surface is a surface of a medical device.

35. The method of forming an adherent, conformable, water-vapor permeable coating on a surface according to claim 34, wherein said medical device is an implantable medical device, a body-adherent medical device, or a medical device that is both implantable and body-adherent.

36. The method of forming an adherent, conformable, water-vapor permeable coating on a surface according to claim 26, further comprising 0.1 to 10 wt % complementary agent, wherein said complementary agent is selected from the group consisting of a plasticizer, an adhesion promoter, an antimicrobial agent, a healing agent, a medicant, and combinations thereof.

37. The method of forming an adherent, conformable, water-vapor permeable coating on a surface according to claim 36, wherein said complementary agent comprises an antimicrobial agent, a medicant, or both; wherein said antimicrobial agent, medicant, or both, contained in said adherent, conformable, water-vapor permeable coating are released to the surface.

38. The method of forming an adherent, conformable, water-vapor permeable coating on a surface according to claim 37, wherein said antimicrobial agent, medicant, or both, are released to the surface at a controlled rate.

39. A kit comprising a liquid, polymer-containing coating material comprising about 1 to 50 wt % amphiphilic polymer and about 50 to 99 wt % of a non-stinging, volatile, hydrophobic liquid as part of a solvent system, said amphiphilic polymer being dissolved in said solvent system; wherein the weight percentages are based on the total weight of the liquid, polymer-containing coating material; wherein said amphiphilic polymer comprises at least one polymerizable nitrogen-containing monomer component whose homopolymer is soluble in water and at least one polymerizable siloxy-containing monomer component that is hydrophobic; wherein said liquid coating material forms an adherent, conformable, water-vapor, water-insoluble permeable coating when applied to a surface, wherein the amphiphilic polymer comprises about 15 to 85 mole % polymerizable nitrogen-containing monomer component and about 15 to 85 mole % polymerizable siloxy-containing monomer component; and wherein said non-stinging, volatile, hydrophobic liquid is a non-stinging, volatile, hydrophobic liquid selected from the group consisting of volatile linear and cyclic siloxanes, volatile alkanes, volatile fluorocarbons, liquid and supercritical carbon dioxide, and mixtures thereof.

40. The kit of claim 39, wherein the liquid, polymer-containing coating material further comprises 0.1 to 10 wt % complementary agent, wherein said complementary agent is selected from the group consisting of a plasticizer, an adhesion promoter, an antimicrobial agent, a healing agent, and a medicant.

41. The liquid, polymer-containing coating material in accordance with claim 1, wherein said hydrophilic polymerizable nitrogen-containing monomer component is selected from the group consisting of polymerizable amides, imides and lactams.

* * * * *